United States Patent
Dillon et al.

(10) Patent No.: US 7,329,353 B2
(45) Date of Patent: Feb. 12, 2008

(54) LC/MS METHOD OF ANALYZING HIGH MOLECULAR WEIGHT PROTEINS

(75) Inventors: Thomas Dillon, Ventura, CA (US); Pavel Bondarenko, Thousand Oaks, CA (US); Gary Pipes, Thousand Oaks, CA (US); Margaret Ricci, Camarillo, CA (US); Douglas Rehder, Woodland Hills, CA (US); Gerd Kleemann, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 409 days.

(21) Appl. No.: 11/040,659

(22) Filed: Jan. 21, 2005

(65) Prior Publication Data
US 2005/0161399 A1    Jul. 28, 2005

Related U.S. Application Data

(60) Provisional application No. 60/548,302, filed on Feb. 27, 2004, provisional application No. 60/538,982, filed on Jan. 23, 2004.

(51) Int. Cl.
*B01D 15/08* (2006.01)
(52) U.S. Cl. .................. 210/635; 210/656; 210/198.2; 250/282; 250/288; 530/413; 530/417
(58) Field of Classification Search ............... 210/635, 210/656, 659, 198.2, 502.1, 85, 96.1; 530/413, 530/417; 250/282, 288
See application file for complete search history.

(56) References Cited

U.S. PATENT DOCUMENTS

| | | | |
|---|---|---|---|
| 3,917,527 A | 11/1975 | Shaltiel | |
| 4,000,098 A | 12/1976 | Hofstee | |
| 4,332,717 A | 6/1982 | Kanaoka et al. | |
| 4,743,680 A | 5/1988 | Mathews et al. | |
| 4,771,128 A | 9/1988 | Ferris et al. | |
| 4,894,439 A | 1/1990 | Dorin et al. | |
| 4,908,434 A | 3/1990 | Mertelsmann et al. | |
| 4,920,196 A | 4/1990 | Aggarwal | |
| 5,252,216 A | 10/1993 | Folena-Wasserman et al. | |
| 5,407,546 A | 4/1995 | Schickle | |
| 5,670,054 A * | 9/1997 | Kibbey et al. | 210/656 |
| 5,872,010 A * | 2/1999 | Karger et al. | 436/173 |
| 6,188,065 B1 | 2/2001 | Takada et al. | |
| 6,621,075 B2 | 9/2003 | Hindsgaul et al. | |
| 6,627,883 B2 | 9/2003 | Wang et al. | |
| 6,642,515 B1 | 11/2003 | Yamaguchi | |

(Continued)

FOREIGN PATENT DOCUMENTS

EP    1 331 266    7/2003

(Continued)

OTHER PUBLICATIONS

Carr et al., Protein Sci., 2:183-196 (1993).

(Continued)

*Primary Examiner*—Ernest G. Therkorn
(74) *Attorney, Agent, or Firm*—Raz Reinecke

(57) ABSTRACT

The present invention is directed to a novel method of analysis of high molecular weight proteins. More specifically, it is directed to a novel reversed-phase LC/MS method of analysis of high molecular weight proteins including antibodies.

4 Claims, 16 Drawing Sheets

U.S. PATENT DOCUMENTS

| | | | |
|---|---|---|---|
| 6,673,253 | B2 | 1/2004 | Moon et al. |
| 6,685,811 | B1 | 2/2004 | Laurin |
| 2001/0034017 | A1 | 10/2001 | Rauth et al. |
| 2002/0146349 | A1* | 10/2002 | Gygi et al. .................... 422/70 |
| 2002/0146838 | A1* | 10/2002 | Singh et al. ................ 436/173 |
| 2002/0155614 | A1 | 10/2002 | Tomlinson et al. |
| 2003/0141253 | A1* | 7/2003 | Bihan ......................... 210/656 |
| 2004/0167320 | A1* | 8/2004 | Couto et al. ................ 530/412 |
| 2005/0161399 | A1* | 7/2005 | Dillon et al. ............... 210/635 |

FOREIGN PATENT DOCUMENTS

| | | | |
|---|---|---|---|
| WO | WO 89/10177 | * | 11/1989 |
| WO | WO-89/10177 | | 11/1989 |
| WO | WO-97/46581 | | 12/1997 |
| WO | WO-01/92510 | | 12/2001 |

OTHER PUBLICATIONS

Grange et al., Spectroscopy, 18(5):12-24 (2003).
Hirota et al., Protein Sci., 6:416-421 (1997).
Saphire et al., Science, 293:1155-1159 (2001).
Whitelegge et al., Protein Sci., 7:1423-1430 (1998).
Aguilar et al., Anal. Chem., 70(23):5010-5018 (1998).
Akashi et al., Anal. Chem., 70(15):3333-3336 (1998).
Alexander et al., Anal. Chem., 67:3626-3632 (1995).
Apffel et al., J. Chromatogr. A, 712:177-190 (1995).
Apffel et al., J. Chromatogr. A, 717:41-60 (1995).
Battersby et al., J. Chromatogr. A, 927:61-76 (2001).
Benedek et al., J. Chromatogr., 317:227-243 (1984).
Benedek, J. Chromatogr., 646:91-98 (1993).
Bongers et al., J. Pharm. Biomed. Anal., 21:1099-1128 (2000).
Boyes et al., J. Chromatogr. A, 691:337-347 (1995).
Brekke et al., Nat. Rev. Drug Discov., 2:52-62 (2003).
Buchner et al., Biochemistry, 30:6922-6929 (1991).
Busch et al., Spectroscopy, 18(5):52-55 (2003).
Chen et al., J. Chromatogr. A, 1010:45-61 (2003).
Cohen et al., Anal. Chem., 56:217-221 (1984).
Cohen et al., Anal. Biochem., 140:223-235 (1984).
Dodonov et al., Rapid Commun. Mass Spectrom., 11:1649-1656 (1997).
Fausnaugh et al., J. Chromatogr., 359:131-146 (1986).
Fenn et al., Science, 246:64-71 (1989).
Geng et al., J. Chromatogr., 296:15-30 (1984).
Guilhaus et al., Mass Spectrom. Rev., 19:65-107 (2000).
Guzzetta et al., Anal. Chem., 65:2953-2962 (1993).
Harris et al., J. Chromatogr. B., 752:233-245 (2001).
Hearn et al., J. Chromatogr., 435:271-284 (1988).
Huddleston et al., Anal. Chem., 65:877-884 (1993).
Josic et al., Food Technol. Biotechnol., 39(3):215-226 (2001).
Karas et al., Anal. Chem., 60:2299-2301 (1988).
Karch et al., J. Chromatogr., 122:171-184 (1976).
Kuwajima, Proteins, 6:87-103 (1989).
Ling et al., Anal. Chem., 63:2909-2915 (1991).
Lu et al., J. Chromatogr., 359:19-29 (1986).
Mant et al., J. Chromatogr. A, 1009:29-43 (2003).
McNay et al., Biotechnol. Bioeng., 76(3):224-232 (2001).
Oroszlan et al., Anal. Chem., 64:1623-1631 (1992).
Ptitsyn et al., FEBS Lett., 262(1):20-24 (1990).
Purcell et al., Anal. Chem., 71:2440-2451 (1999).
Purcell et al., J. Chromatogr. A, 711:71-79 (1995).
Richards et al., J. Chromatogr. A., 676:17-31 (1994).
Richards et al., J. Chromatogr. A., 676:33-41 (1994).
Tanaka et al., Rapid Commun. Mass Spectrom., 2(8):151-153 (1988).
Velicelebi et al., Biochemistry, 18(7):1180-1186 (1979).
Vidal-Madjar et al., J. Chromatogr., 548:81-91 (1991).
Winkler et al., J. Chromatogr., 347:83-88 (1985).
Le et al., Am. Soc. Mass Spectrom., 16:307-311 (2005).
International Search Report in PCT/US2005/001840 dated Oct. 13, 2005.

\* cited by examiner

LC/MS METHOD OF ANALYZING HIGH MOLECULAR WEIGHT PROTEINS

The present application claims the benefit of priority under 35 U.S.C. §119 of U.S. Provisional Patent Application No. 60/538,982 filed Jan. 23, 2004 and U.S. Provisional Patent Application No. 60/548,302 filed Feb. 27, 2004. The entire text of each of the foregoing applications is incorporated herein by reference.

BACKGROUND

1. Field of the Invention

The present invention is generally directed to LC/MS analysis of high molecular weight proteins, including antibodies and antibody conjugates or fragments.

2. Background of the Related Art

Purification techniques such as high performance liquid chromatography (HPLC) that are readily adaptable for the separation and analysis of low molecular weight species often have limited application when being used to separate protein species larger than 50 kDa. In addition, the characterization and/or consistency of manufacture of a given protein often relies on peptide mapping in order to monitor the amino acid sequence and/or conformational properties of the protein being analyzed. While peptide mapping and analysis of intact proteins are able to detect small changes in small- to moderate-sized proteins, for example, insulin (molecular weight 6 kDa) and human hormone of molecular weight 22 kDa (Oroszlan et al., *Anal. Chem.*, v. 64, p. 1623-1631, 1992), this kind of detailed analysis of a larger protein, for example, heterogeneous glycoproteins such as antibodies (150 kDa) requires cleavage of these proteins into a large number of peptides. The analysis of these larger proteins by peptide mapping is thus, hindered by the complexity of the range of peptides generated by timely enzymatic digestion or non-specific catalytic or hydrolytic digestion of the protein and separation of the multiple peptides. Therefore, reversed-phase (RP) HPLC of large proteins is an attractive alternative approach to peptide mapping, because the former method often does not require any sample preparation and is relatively simple in data interpretation.

In 1984 (Geng and Regnier, *J. Chromatogr.*, v. 296, p. 15-30, 1984), a retention model was proposed for proteins in reversed-phase HPLC incorporating three processes: adsorption, solvation and desorption. According to the model, protein elution is a result of a stoichiometric displacement of protein on the alkyl-bonded surface by molecules of organic solvent. In that study, iso-propanol was identified as a stronger displacing agent as compared to methanol and ethanol. The paper also suggested that change of chromatographic retention with temperature is governed by altering both the forces of interaction between molecular species (the forces of attraction between all the components decrease with increasing temperature) and the protein conformation (Geng and Regnier, *J. Chromatogr.*, v. 296, p. 15-30, 1984).

Other efforts to improve RP-HPLC separation of large proteins included optimization of the n-alkyl silica phase, mobile phase, column temperature and pore size. Nevertheless, there remains a significant problem in RP chromatography of large proteins in that a single protein generally produces broad, asymmetrical and even multiple chromatographic peaks at near-room temperatures. These phenomena have previously been documented in several reports (Cohen et al., *Anal. Biochem.*, v. 140, p. 223-235, 1984a; Cohen et al., *Anal. Chem.*, v. 56, p. 217-221, 1984b,; Hearn et al., *J. Chromatogr.*, v. 435, p. 271-284, 1988; Lu et al., *J. Chromatogr. A*, v. 359, p. 19-29, 1986; Oroszlan et al., *Anal. Chem.*, v. 64, p. 1623-1631, 1992; Purcell et al., *Anal. Chem.*, v. 71, p. 2440-2451 1999a; Richards et al., *J Chromatogr. A*, v. 676, p. 33-41, 1994; Richards et al., *J. Chromatogr. A*, v. 676, p. 17-31, 1994) and may be related to partially unfolded conformational intermediates trapped on the stationary phase under gradient elution conditions.

Mass spectrometry is a powerful technique for characterization of proteins including large proteins. A mass spectrometer includes two main components: 1) ion source, which desorbs protein molecules from liquid or solid state into the gas phase and ionizes them and 2) mass analyzer, which determines the molecular weight values of the protein ions. Electrospray ionization (ESI), (Fenn et al., *Science*, 246, 64, 1989) and matrix-assisted laser desorption/ionization (MALDI), Karas and Hillenkamp, *Anal. Chem.* 60, 2299 (1988); Tanaka et al., *Rapid Communications in Mass Spectrometry*, 2, 151-153 (1988), are the two most powerful modern ion sources for protein analysis by mass spectrometry. In these sources, a positively charged protein ion is formed by attaching one or several protons to the molecule of protein. Ion trap (IT), quadrupole (O), magnetic sector, Fourier transform ion cyclotron resonance (FT-ICR), time-of-flight (TOF) and orthogonal time-of-flight (orthogonal TOF) are the mass analyzers typically employed for proteins analysis. These analyzers produce mass spectrum with m/z values of detected ions on x-axis and ion intensity on y-axis. MALDI typically produces ions with low charge. For example, a 150 kDa (m) antibody typically produces ions with +1, +2 and +3 charges (z) and m/z values of 150 kDa, 75 kDa and 50 kDa, correspondently, Akashi et al., *Anal. Chem.* 70(15):3333-6, 1998; Alexander and Hughes, *Anal. Chem.* 67 (20):3626-32, 1995.

The TOF and orthogonal-TOF analyzers posses the largest m/z scale and most suitable for the large protein analysis. It was found that detection efficiency of the protein ions decreases with increasing their m/z values. The ESI is more efficient ionization technique, which produces multiply charged ions with large number of charges (z) significantly reducing their m/z range and improving their detection efficiency. Typically, larger proteins will produce ions with larger m/z values. For example, one of the advantages of ESI source as compared to MALDI is that the former is suitable for in-line operation with HPLC. In the ESI source, the proteins eluting from an HPLC column are ionized and ejected into the gas at atmospheric pressure. Then the ions are guided into the vacuum through an atmosphere-vacuum interface into the mass analyzer. The orthogonal TOF analyzers were found to be a good choice for the LC/MS analysis, because it transforms the continuous flow of ions from the ESI source into the pulsed beam required for TOF analysis using an orthogonal accelerator Dodonov et al., *Rapid Comm. Mass Spec.* 11(15):1649-56, 1997; Guilhaus et al., *Mass Spec. Rev.* 19(2):65-107, 2000. Taking into account the above considerations, the ESI orthogonal TOF mass spectrometer is currently the best choice for LC/MS analysis of large proteins. The other mass analyzers, such as the listed above (IT, Q, FT-ICR, magnetic sector) are also applicable after appropriate tuning.

The discovery that multiply charged ions produced by electrospray mass spectrometry (ESI-MS) can be deconvoluted to determine the molecular mass of a protein with masses in excess of the conventional m/z range of a mass spectrometric analyzer has led to the use of ESI-MS for the analysis of protein structures (see discussion in Fenn et al., *Science* 246, 64, 1989). ESI-MS has been successfully used to analyze proteins having a MW of approximately 50 kDa (see Whitelegge et al., Protein Sci. 1998 June; 7(6):1423-30, 1998, presenting analysis of intact membrane proteins of MW of 42 kDa). While mass spectrometry has been used for the analysis of small protein fragments of less than 90 kDa, the applicability of mass spectrometry for the analysis of higher molecular weight proteins has not been effectively achieved.

In addition to the use of HPLC and MS separately, commercially available combined HPLC and electrospray ionization mass spectrometry (LC-ESI-MS) systems compatible with conventional HPLC has proven useful in peptide mapping (Ling et al., Anal. Chem., 63: 2909-2915, 1991; Guzzetta et al., Anal. Chem., 65: 2953-2962, 1993; Bongers et al., J. Pharm. Biomed. Anal., v. 21, p. 1099-1128., 2000). LC-ESI-MS in combination with in-source collisionally induced dissociation (CID) has been used effectively to identify sites of N- and O-linked glycosylation, but again this methodology is only effective with peptides or small protein fragments (Carr et al., Protein Sci., 2: 183-196, 1993; Huddleston et al., Anal. Chem., 65: 877-884, 1993; Conboy and Henion, J. Am. Soc. Mass Spectrom., 3: 804-814, 1992). However, these techniques remain inadequate for analysis of antibodies and other large conformationally complex proteins. This is due to an insufficient resolution resulting from the confounding effects of the large numbers of very similar peptides that result from variable protein glycosylation and enzymatic digests of moderately sized glycoproteins. It is therefore necessary to employ a range of techniques with orthogonal selectivity to characterize such samples.

The use of combinations of high-performance capillary electrophoresis, HPLC, LC-ESI-MS, and matrix-assisted laser desorption ionization-time of flight mass spectrometry has been investigated to allow for characterization of enzymatic digests of underivatized glycoprotein samples, as exemplified by DSPα1, a single-chain plasminogen activator derived from vampire bat salivary glands (Apffel et al, J. Chromatography A, 717: 41-60, 1995). It was concluded that these four techniques when used in combination are complimentary techniques for examining glycoproteins, although only on protein digests rather than on high molecular weight proteins. Nonetheless, the authors acknowledged that more work needs to be done to improve the power of this approach, and that high-yield concentration steps will be required due to extensive carbohydrate heterogeneity.

Thus, useful information from the LC-ESI-MS or MALDI-TOF techniques can only be obtained from analysis of intact proteins that are relatively small, e.g., less than 10 kDa. Although the peptide mapping can be used to obtain the more detailed information, this method consumes a lot of time for sample preparation and data interpretation and becomes very complicated when molecular weight of protein increases. However, many biologically-relevant proteins have higher molecular weights and further, have post-translational modifications that can confound their analyses in mass spectrometry and/or HPLC. Thus, despite the fact that there are techniques that have been extensively used in the analysis of low molecular weight proteins such as insulin, or low molecular weight digests of larger proteins, there remains a need for additional methods and techniques for producing sequence and detailed conformational information about proteins.

SUMMARY OF THE INVENTION

The present invention is directed to new LC/MS methods for the analysis and quantification of high molecular weight proteins. In a specific embodiment the present invention is directed to a method for analysis of a protein in a sample comprising preparing a sample comprising the protein for loading onto a high performance liquid chromatography (HPLC) column; separating the high molecular weight protein from the sample by reversed-phase HPLC on the column, wherein the HPLC column is heated to a temperature of from about 50° C. to about 90° C.; and wherein the mobile phase of the reversed-phase HPLC comprises a water miscible organic solvent having a C18 eluotropic strength coefficient of at least 6.0 and detecting the presence of the protein in an eluate from step of the HPLC step. In certain embodiments, detecting the presence of the protein in an eluate may be performed by a UV, visible light or fluorescence detector. Where UV detection is employed, the UV cutoff of the solvent can be one which allows the solvent to be used in UV detection of proteins especially at e.g., 215 nm, 245 nm or 280 nm. In another embodiment, the protein has a molecular weight of at least 90 kDa.

The detecting may advantageously be carried out using any technique normally used for the detection of proteins. For example, the detection may comprise UV detection of the eluate. UV detection at 215 nm, 245 nm or 285 nm is particularly contemplated. In a particular embodiment, the detection method comprises introducing the eluate from the HPLC into the ion source of a mass spectrometer and determining the molecular weight of the high molecular weight protein by mass spectrometry. More preferably, the mass spectrometer is an electrospray mass-spectrometer (ESI-MS) that is in-line with the HPLC column. The method may further comprise identifying the presence or absence of a particular carbohydrate moiety on the high molecular weight protein by comparing its empirically determined molecular weight to the to the calculated molecular weights of the protein portion plus known standard carbohydrate moieties. For example, the presence or absence of a particular carbohydrate moiety on the high molecular weigh protein is determined by comparing the molecular weight data of the high molecular weight protein determined from the RP-HPLC/MS analysis to theoretical amino acid sequence of said protein with attached carbohydrate moieties or other known post-translational modifications.

In a particular embodiment, the solvent employed in the mobile phase comprises an organic solvent having a C18 eluotropic strength coefficient of at least 8.0. For example, the organic solvent may have a C18 eluotropic strength coefficient of at least 10.0. Typically, such a solvent may be an alcohol having between 2 and 4 carbon atoms. Thus, examples of solvents useful in the mobile phase of the present invention include alcohols selected from the group consisting of n-propanol, isopropanol, n-butanol and isobutanol. Another solvent that may be useful is dioxane. It is contemplated that in certain embodiments, ethanol may also be used.

The stationary phase for the RP-HPLC methods of the invention may be any stationary phase typically employed for the separation of proteins. In exemplary embodiments, the RP-HPLC column comprises a silica-based stationary phase that is derivatized with an alkyl group. Preferably, the alkyl group is selected from a C3 to C18 alkyl group. In specific embodiments the preferred alkyl group is either a C8 or C18 alkyl group. C3 alkyl groups also may be used as part of the stationary phase. In particular embodiments, the C8 alkyl group is derivatized with a diphenyl group. In other embodiments, the stationary phase comprises a C3 alkyl group that is derivatized with a cyano group. In certain circumstances, it may be possible to employ a stationary phase that comprises a mixture of alkyl groups.

The RP-HPLC method described herein may advantageously be carried out at a pH of between about pH 1.0 to about pH 6.0. Preferably, the pH of the mobile phase is between about pH 1.0 to about pH 3.0.

In preferred embodiments, the mobile phase has a concentration that comprises at least 15% isopropanol at the time of elution of the protein.

As discussed herein throughout, the methods of the invention employ an in-line, ESI-MS. Preferably, the ESI-MS comprises a time-of-flight mass analyzer. More preferably, the ESI-MS is an orthogonal time-of-flight (TOF) ESI-MS. In preferred embodiments, the mass spectrometer has a mass resolution of at least 3000.

The RP-HPLC may be performed using gradient elution or isocratic elution. In those embodiments employing isocratic elution, the mobile phase is an isocratic mobile phase comprising at least 20% isopropanol and having an acidic pH. More preferably, the mobile phase is an isocratic mobile phase comprising at least 50% isopropanol and having an acidic pH. Other embodiments employ a mobile phase is an isocratic mobile phase comprising at least 70% isopropanol and having an acidic pH. In those embodiments employing gradient elution, the mobile phase comprises a gradient of isopropanol from 5% isopropanol to 90% isopropanol, wherein the gradient is established over a period of one hour. In other embodiments, the mobile phase comprises a gradient of isopropanol from 10% isopropanol to 60% isopropanol, wherein the gradient is established over a period of one hour.

In specific embodiments, the gradient is established comprising introducing a mixture of a first solvent A and a second solvent B as the mobile phase for said HPLC, wherein said first solvent A comprises a mixture at pH 2.0 of water and trifluoracetic acid (TFA) and said second solvent B comprises a mixture at pH 2.0 of 70% isopropanol, 20% acetonitrile 9.9% water and 0.1% TFA.

The analytical methods of the present invention have the particular advantage of being applicable to high molecular weight proteins. In one embodiment, the molecular mass of the high molecular weight protein being analyzed is at least about 90 kDa. These proteins can include a single polypeptide chain that has a weight as determined by standard sodium dodecyl sulfate-polyacrylamide gel electrophoresis (SDS-PAGE), but can also include proteins that are multimers, e.g., two or more proteins that associate via protein interaction domains or disulfide linkages. These multimers can have subunits that are less than 90 kDa, but when combined in a complex form a molecule having a calculated molecular weight in excess of 90 kDa. One specific example is an antibody. Indeed, in an exemplary embodiment of the invention, the high molecular weight protein is an antibody. In additional embodiments, the methods of the invention are directed to analysis of portions of an antibody, such as e.g., an Fab, Fc, heavy chain (HC) and light chain (LC) regions of an antibody or combinations thereof which may comprise a molecular weight less than 90 kDa (e.g., such antibody derived fragments have a molecular weight of 45 kDa, 50 kDa, 55 kDa, 60 kDa, 65 kDa, 70 kDa, 75 kDa 80 kDa, 85 kDa or more). The antibody derived fragments may be derived through proteolytic cleavage or chemical cleavage.

In still further embodiments, the high molecular weight protein may be a chimeric molecule that comprises an antibody protein portion and a non-antibody protein portion. The antibody protein portion of such a chimeric molecule may include, but is not limited to, an Fab, Fc, heavy chain (HC) and light chain (LC) regions of an antibody or combinations thereof, and the non-antibody portion of such a chimeric molecule may comprise any non-antibody peptide or protein.

A particular aspect of the present invention is directed to a method for analyzing an antibody or a fragment thereof, the method comprising preparing a sample comprising the antibody or fragment thereof for loading onto a high performance liquid chromatography (HPLC) column; separating the antibody or fragment thereof from the sample by reversed-phase HPLC on the column, wherein the eluate from the reversed-phase HPLC is introduced into the ion source of a mass spectrometer, wherein the mass spectrometer is in-line with the HPLC column; and obtaining mass fragmentation data of the antibody or fragment thereof by mass spectrometry; wherein the HPLC column is heated to a temperature of from about 50° C. to about 90° C.; and wherein the mobile phase of the reversed-phase HPLC comprises a water miscible organic solvent having a C18 eluotropic strength coefficient of at least 6.0. Preferably, the UV cutoff of the solvent is one which allows the solvent to be used in UV detection of proteins especially at 215 nm, 245 nm or 280 nm.

An antibody comprises a constant domain and two variable regions. More particularly, in exemplary embodiments, an antibody analyzed in the methods of the invention is of an IgG class selected from the group consisting of IgG1, IgG2, IgG3, and IgG4. The method of the invention also contemplates analysis of an antibody that is a single chain antibody, e.g., scFv. In alternative embodiments the methods of the invention are used to analyze a humanized antibody. In particular embodiments, the antibody is a humanized IgG2 antibody. In yet further embodiments, the methods of the invention are used to analyze fusion proteins or human or humanized antibodies.

The RP-HPLC analysis of the present invention of a protein further comprises subjecting the protein to cleavage by limited proteolysis or chemical cleavage. Preferably, the limited proteolysis is conducted prior to loading the sample on the HPLC column. In more particular embodiments, the limited proteolysis comprises digestion with an enzyme during a relatively short period of time, typically less than 1 hour. In another embodiment, the chemical cleavage was performed by reducing the disulfide bonds in the protein or fragments thereof. For example, the reduction of the disulfide bonds comprises contacting the sample with a reducing agent. Exemplary reducing agents include but are not limited to dithiothreitol, mercaptoethanol, tributylphosphine, and tri(2-carboxyethyl)phosphine hydrochloride. Alternatively, the protein may be subjected to chemical cleavage. As an alternative to chemical cleavage, the methods of the invention also contemplate enzymatic proteolysis using enzymes such as papain, pepsin, or Lys-C protease.

The methods of analyzing the proteins described herein will be particularly useful in determining the structural integrity of a protein. Thus, the RP-HPLC/MS methods of the invention specifically contemplate determining the presence of a protein degradation product in an antibody sample, the method comprising performing RP-HPLC on the protein under conditions wherein the HPLC column is heated to a temperature of from about 50° C. to about 90° C.; and wherein the mobile phase of the reversed-phase HPLC comprises a water miscible organic solvent having a C18 eluotropic strength coefficient of at least 6.0, and determining the molecular weight data of the protein using ESI-MS. Comparing the molecular weight data from the protein to data generated from known standards may be an effective method of determining the presence of any degradation products. For example, performing the method on an antibody sample known not to have undergone degradation will provide an effective standard against which to measure the data produced from an antibody sample that is being tested for degradation products as the presence of degradation products will be detectable as differences compared to the measurements produced by the standard. Likewise, molecular weight profiles may be generated for common moieties normally present and change in molecular weight values thereof due to e.g., alteration or loss may be indicative of degradation. Similarly, profiles of dimer formation, cleavage product, oxidation, deamidation, N-terminal pyroglutamation and disulfide bond scrambling may be generated or known to those of skill in the art and the presence of such a profile may be indicative of the degradation.

In certain preferred embodiments, the methods described herein may be used as methods of determining disulphide bond rearrangement of an IgG2 sample, where the method comprises performing RP-HPLC on the IgG2 sample under conditions wherein the HPLC column is heated to a temperature of from about 50° C. to about 90° C.; and wherein the mobile phase of the reversed-phase HPLC comprises a water miscible organic solvent having a C18 eluotropic strength coefficient of at least 6.0; detecting the presence of heterogeneous peaks from the RP-HPLC of the IgG2 sample; and determining the molecular weight data of the components of the heterogeneous peaks of the RP-HPLC of the IgG2 sample using ESI-MS, wherein identical or similar molecular weight data is indicative of disulfide bond rearrangement in the IgG2 sample. In more specific embodiments, the disulphide bond rearrangement may be monitored as a mass difference of two mass units.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

The following drawings form part of the present specification and are included to further illustrate aspects of the present invention. The invention may be better understood by reference to the drawings in combination with the detailed description of the specific embodiments presented herein.

DESCRIPTION OF THE PREFERRED EMBODIMENTS

Figure 1:
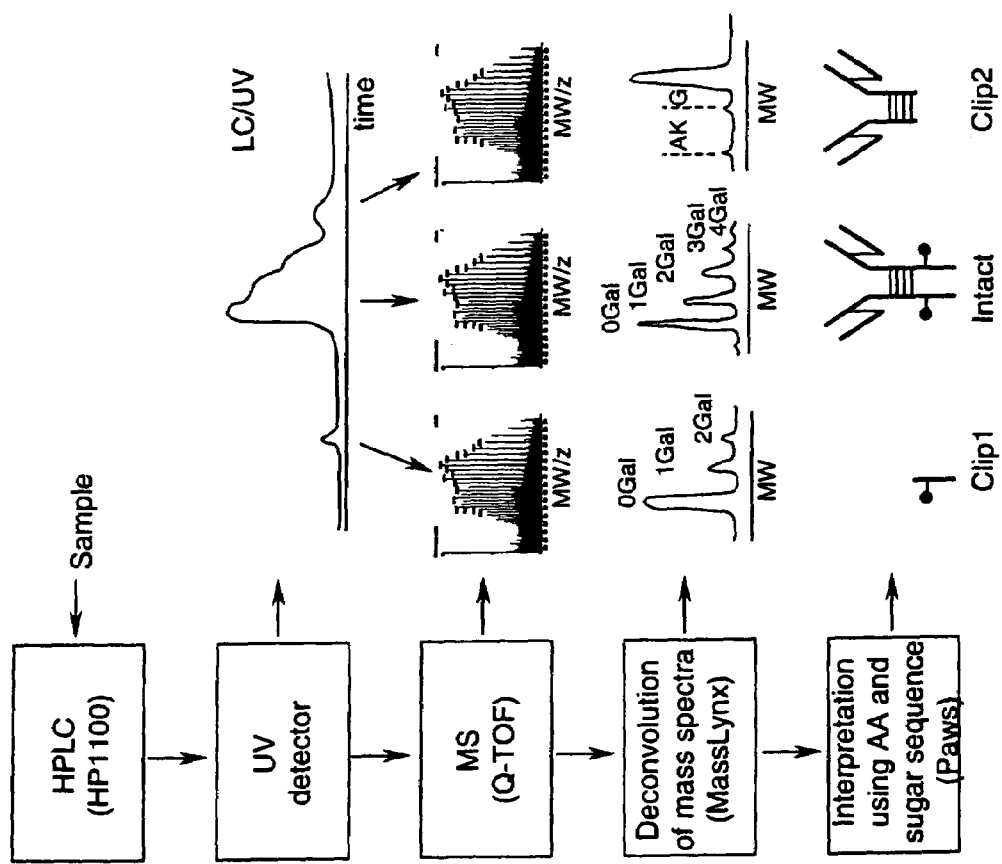
FIG. 1. Schematic of LC/MS method of analysis for large proteins. A protein sample is injected on a RP column operated under high temperature and eluted in a high percentage of isopropanol to separate and quantify the sample fractions. A high resolution mass spectrometer (Q-TOF) is connected to the HPLC system (HP1100) using electrospray ionization interface to generate mass spectra of multiply charged ions with different numbers of charges (z) attached. These mass spectra are deconvoluted into MW values using MassLynx software. The sample fragments are identified by correlating the measured MW data, sugar patterns and terminal amino acid sequences (if additional terminal cleavages take place) with anticipated amino acid and oligosaccharide sequences.

The present invention is directed to addressing a need for methods of analyzing high molecular weight proteins (e.g., antibodies) without the need for an initial step of producing smaller molecular weight protein digests. Prior to the present invention, RP-HPLC was inadequate for the analysis of high molecular weight proteins (e.g., antibodies) due to the fact that such proteins produced broad peaks with long tails that were a result of partial unfolding of the protein on the column. The methods of the present invention are used to achieve a conformational homogeneity of the protein being analyzed by unfolding the protein during the chromatographic separation, so that any covalent modifications may be clearly identified.

In particular embodiments, the present invention describes a method of analyzing a protein sample using a combined HPLC-MS technique in which the HPLC separation is performed in-line with the MS analysis. Specifically, the HPLC apparatus is directly connected to the mass spectrometer, wherein the mass spectrometer directly receives the separated products from the HPLC column. More particularly, the methods of the invention employ a combination of high-temperature column RP-HPLC separation with the use of a high percentage of a water miscible organic solvent that has a C-18 eluotropic strength coefficient of at least 6.0. It is found herein that by use of this combination, high molecular weight proteins may be analyzed and quantified without the necessity of producing smaller protein digests.

In specific embodiments, the present invention contemplates the combined use of a reversed-phase HPLC method with UV and MS detection for determining the molecular weight and integrity of IgG1 and IgG2 classes of antibodies. The RP-HPLC method uses high column temperatures, mobile phase with eluotropic coefficient above 6 and silica stationary phases with alkyl chains from C3 to C18, which may or may not be further derivatized with e.g., cyano and diphenyl derivatives. The methods of the invention typically may be used to analyze antibodies or fragments of antibodies (e.g., products of disulfide bond reduction, proteolytic or chemical cleavage). The antibody fragments can be any size. Preferably, the antibody fragments are four fragments (two light chains (25 kDa each) and two heavy chains (50 kDa each)) produced by reduction or alternatively or are fragments (Fc (50 kDa), and Fab(50 kDa)) produced by limited proteolysis.

Protein fragments as used herein are fragments of a large protein created by cleaving the protein using limited proteolysis with an enzyme or chemical cleavage by reducing the disulfide bonds. For example, an IgG1 antibody can be effectively cleaved by Lys-C protease to generate Fc domain (50 kDa) and two Fab domains (50 kDa each) over a short time period below 1 hour. An IgG2 antibody can be cleaved with pepsin protease to generate Fc domain (50 kDa) and (Fab)$_2$ domain (100 kDa). An IgG1 or IgG2 antibody can be reduced to produce two light chains (25 kDa each) and two heavy chains (50 kDa each). These examples illustrate that the above methods produce antibody fragments, which are, in general, larger than 20 kDa. In contrast to fragments, peptides are products of enzymatic cleavage of proteins into peptides with typical sizes from 0.5 kDa to 5 kDa over a time period typically from 4 hours to 24 hours. As used herein, the term "proteolysis" has a standard definition and is used to describe the hydrolytic breakdown of proteins into simpler, soluble substances such as peptides and amino acids.

In exemplary embodiments, the methods of the invention use an HPLC system in-line with an ESI-TOF mass spectrometer utilizing MassLynx software for data processing. FIG. 1 shows a schematic of an exemplary method of analysis according to the present invention. A protein sample to be analyzed is injected onto a RP column operated under high temperature and eluted with a high percentage of a water-miscible organic solvent that has a high C18 eluotropic strength coefficient to separate the sample into components, quantify the components with a U.V. detector (preferably and in-line U.V. detector) and identify the components using an in-line mass spectrometer. A high resolution mass spectrometer connected in-line to the HPLC apparatus generates mass spectra of multiply charged ions with different numbers of associated charges (z). These mass spectra are deconvoluted into protein MW values using software such as, e.g., MassLynx.

The sample components are quantified by using UV detector and identified by correlating the measured MW data, sugar patterns and partial terminal sequences with standard data generated for amino acid sequences and oligosaccharide structures. Relative abundances of the glycoforms are calculated from the peak intensities in the mass spectra, e.g. in FIG. 3B. The terminal sequences also may be identified by the mass spectrometry by reviewing the data for minor cleavages that occur in the vicinity of the main cleavage (See Example 2) for further details. The techniques used in the methods of the invention and variations thereof are described in further detail herein below.

Reversed-Phase High Performance Liquid Chromatography (RP-HPLC)

RP-HPLC has become a widely used, well-established tool for the analysis and purification of biomolecules. The popularity of this technique for use in analyzing and purifying proteins and peptides is due to the resolution it is able to provide. Further, unlike other widely used protein analysis techniques such as e.g., size exclusion chromatography, capillary electrophoresis and ion exchange chromatography, RP-HPLC is particularly attractive for the analysis of proteins in that it is readily adapted for use with in-line mass spectrometry.

RP-HPLC is able to separate polypeptides of nearly identical sequences, not only for small peptides such as those obtained through trypsin digestion, but even also for proteins as large as 5,300 Da (e.g., insulin). Compounds adsorb to the reversed-phase stationary phase in high aqueous mobile phase and are eluted from RP HPLC columns with increasing organic mobile phase. In RP-HPLC, compounds are separated based on their hydrophobic character. Peptides (typically 10 to 30 amino acid residues in length) can be separated by running a linear gradient of the organic solvent. Typically in a simple 60/60 gradient (starting at 100% aqueous (elution solvent A) ramping to 60% organic solvent (elution solvent B) in 60 minutes) the majority of peptides will elute by the time the gradient reaches 30% organic. In the present invention, the inventors have found that the use of a high percentage of a suitable organic solvent in combination with a high column temperature will facilitate the analysis of proteins of molecular weight greater than 10,000 Da. The present section provides a discussion of the exemplary solvents, stationary phase and column temperatures that may be used in the present invention.

General sources for HPLC apparati and components are well known to those of skill in the art. For example, all types of HPLC equipment, supplies and components are commercially available from Agilent (Palo Alto, Calif., e.g., the 1100™ standard and capillary HPLC's); Alltech Associates Inc., (Deerfield, Ill.) Bodman (Aston, Pa.); Cohesive Technologies (Franklin, Mass.; specializing in systems for chromatographic solutions for pharmacokinetic analysis), LC Packings (Sunnyvale, Calif.; vendors of capillary HPLCs, columns and capillary UV flow cells); Michrom BioResources, Inc. (Auburn, Calif., vendors of the MAGIC 2002™ HPLC plus columns traps and other HPLC and LC/MS supplies and accessories); Micro-Tech Scientific Inc. (Sunnyvale, Calif.; vendors of capillary HPLCs along with a large selection of capillary HPLC columns and supplies); Rheodyne L. P. (Pohnert Park, Calif.; suppliers of HPLC injection valve and other components of basic HPLC equipment); ThermoFinnigan (Woburn, Mass.; suppliers of Surveyor™ HPLC, UV detectors and autosamplers); Waters Corporation (Milford, Mass., suppliers of HPLCs machines, HPLC columns, mass spectrometers); Upchurch Scientific (Oak Harbor, Wash., suppliers of chromatography products and specialize in HPLC fittings and connections); Valco Instruments Co. Inc. (Houston, Tex.; HPLC injection valves; injectors, detectors, valves, fittings, syringes and tubing) and Vydac (Columbia Md. vendors of HPLC columns ranging from capillary to preparative columns, e.g., Vydac C8-300A-5 micron may typically be used for peptide separation).

a. Temperature

Higher temperatures of RP columns (sometimes above 75° C. (Mant et al., *J. Chromatogr. A*, v. 1009, p. 45-59, 2003; Purcell et al., *Anal. Chem.*, v. 71, p. 2440-2451, 1999; Richards et al., *J. Chromatogr. A*, v. 676, p. 33-41, 1994; Richards et al., *J. Chromatogr. A*, v. 676, p. 17-31, 1994) were employed to completely and irreversible unfold proteins, eliminate multiplication of peaks and improve peak shape. In conventional RP-HPLC, partially unfolded peptide species produce broad chromatographic peaks, which can be rendered narrower and more discrete by elevating the column temperature.

The retention of peptides on a RP-column is particularly sensitive to structural changes that occur at, or near, the interactive binding region on the surface of the protein. In amphipathic α-helical peptides (Mant et al., *J. Chromatogr. A*, v. 1009, p. 29-43, 2003) and α-helical coiled-coils (Mant et al., *J. Chromatogr. A*, v. 1009, p. 45-59, 2003), temperature profiling was used to monitor dissociation of dimers at lower temperatures and unfolding of monomeric α-helices at higher temperatures. Further beta-sheets may be formed after partial unfolding of protein, leading to dimerization or enhanced hydrophobic interaction with n-alkyl silica stationary phase. These species typically generate post-peaks. An immunoglobulin G (IgG) antibody contains multiple domains with a similar structure of two beta sheets packed tightly against each other in a compressed antiparallel beta barrel, so the proposed dimerization and enhanced hydrophobic interaction with the ligands causes such molecules to be retained on the column and to be eluted over a longer period of time. The present inventors have discovered that increasing the temperature of the HPLC column to 50° C. or greater in combination with the use of strong eluotropic strength RE-HPLC solvents (discussed below) allows the elution of the Ig molecule in a more discrete fashion.

Thus, in the methods of the present invention it is contemplated that RP-HPLC step of the in-line RP-HPLC/MS is performed at a temperature of at least 50° C. The HPLC may be performed at other temperatures e.g., at 55° C., 60° C., 65° C., 70° C., 75° C., 80° C., 85° C., 90° C. or greater temperatures. It should be understood that these listed temperatures merely provide exemplary embodiments of the column temperature, and those of skill in the art would understand that any individual numerical amount between about 50° C. and 90° C. is particularly contemplated and each of the individual values between this range is specifically intended to be within the scope of the invention, and each individual value between this range has not been recited simply for ease of legibility and not because it was intended to be excluded from the scope of the application.

It is particularly contemplated that the column temperature of the RP-HPLC step may be kept at the elevated temperature throughout the whole RP-HPLC separation step. Alternatively, it also is contemplated that the elevated temperature may be used for only part of the RP-HPLC separation step. For example, as discussed herein below, RP-HPLC typically employs a gradient of organic solvent and the methods of the present invention employ specific organic solvents that have a high C-18 eluotropic strength coefficients, it is contemplated that the RP-HPLC may advantageously be performed by elevating the column temperature at that time at which the percentage of the organic solvent reaches a specific percentage. Alternatively, where the RP-HPLC is performed isocratically, the column temperature may be elevated after a preset time.

HPLC column heaters are readily commercially available from e.g., Timberline H-101 HPLC column heater from Timberline Instruments Inc. (Boulder, Colo.), the Ambient Temperature Controller ATC 10/75 and Advanced Heater Cooler AHC 0/100, both available from Chrom-Tech; Spectra Physics supplies a Model 748 Large Size HPLC Column Heater with Temperature Controller, Shimadzu Scientific Instruments, Inc. manufacture a Model CTO-10A Column Oven, Flatiron Systems, Inc.—Model CH-30 Column Heater, and Eldex Labs, Inc.—Model 725-1010 Column Heater with 44-38 Controller. Any such exemplary column heaters may be used to achieve the desired column temperatures discussed herein.

b. Stationary Phase

Although in general reversed-phase LC/MS analysis is widely used for characterization of peptides and small proteins, this method has had only limited success in applications to large proteins including antibodies. The reversed-phase chromatographic method has been often considered to be a bad choice for large proteins due to the poor peak shape and recovery from the column. The peak shape and recovery of antibodies was recently improved by employing POROS reversed-phase stationary phase with water-acetonitrile-TFA mobile phase and column temperatures elevated to 75° C. (Battersby et al., J. Chromatogr. A, v. 927, p. 61-76, 2001). Although POROS columns produce narrow peaks without tailing, this technique suffers from the following two limitations. First, a relatively small value of selectivity factor (α), determined by the low surface density of POROS material, will limit separation of structural variants and degradation products with similar retention properties. Second, the high flow rate required for efficient separation on POROS columns reduces sensitivity of the online mass spectrometric detection. The conventional mobile phases including water/acetonitrile/TFA were used and mass spectrometry was not applied to identify intact proteins in that study (Battersby et al., J. Chromatogr. A, v. 927, p. 61-76, 2001). The chromatographic separation suffered from the above two limitations of the POROS columns.

The stationary phase of the RP-HPLC steps of the present invention will have to be one which can withstand the elevated temperatures with low pH at which the separation is performed. It is known that the ligand characteristics of the sorbent may significantly influence the nature of the interactive structure of protein (Purcell et al., *Anal. Chem.*, v. 71, p. 2440-2451, 1999). The use of an N-butyl (C4) column matrix has been compared to n-octadecyl (C18) sorbent (Aguilar et al., *Anal. Chem.*, v. 70, p. 5010-5018, 1998; McNay and Fernandez, *Biotechnol. Bioeng.*, v. 76, p. 224-232, 2001; Purcell et al., *J. Chromatogr. A*, v. 711, p. 71-79, 1995; Purcell et al., *Anal. Chem.*, v. 71, p. 2440-2451, 1999; Richards et al., *J. Chromatogr. A*, v. 676, p. 17-31, 1994); C8 and CN were compared in (Boyes and Walker, *J. Chromatogr. A*, v. 691, p. 337-347, 1995; Mant et al., *J. Chromatogr. A*, v. 1009, p. 29-43, 2003), and a greater extent of unfolding is seen with the C18 sorbent as compared to the C4-bounded stationary phase due to the lower hydrophobicity of the latter matrix (McNay and Fernandez, *Biotechnol. Bioeng.*, v. 76, p. 224-232, 2001). In the described case, the radius of curvature inside the pore approaches the size of the separated molecule. Further, there is a distinct hydrolytic stability of columns towards the low pH and elevated temperature in stericaly-protected C18 and C8 packing materials (Boyes and Walker, *J. Chromatogr. A*, v. 691, p. 337-347, 1995; Aguilar et al., *Anal. Chem.*, v. 70, p. 5010-5018, 1998; Chen et al., *J. Chromatogr. A*, v. 1010, p. 45-61, 2003; Mant et al., *J. Chromatogr. A*, v. 1009, p. 29-43, 2003). In the present invention, it is demonstrated that the RP-HPLC/MS produces that most effective separation and analyses when performed using a C8 or C18 column. In preferred embodiments, the Zorbax SB C8 or C18 columns are used. However, it should be understood that any comparable C8 or C18 RP-HPLC column may be used. Such columns are readily available from the commercial sources listed herein above.

Typically, the columns used in the methods of the present invention comprise a silica-based packing material that is derivatized for use in a RP-HPLC column. Such materials and methods of making the same are well known to those of skill in the art. In preferred embodiments, the silica is derivatized with alkyl moieties. The alkyl moiety may be any moiety that can be used in a RP-HPLC separation technique. It is particularly contemplated that the silica is derivatized with a C3, C4, C5, C6, C7, C8, C9, C10, C11, C12, C13, C14, C15, C16, C17 or C18 moieties. In particular embodiments, the column is a C18 column. In other embodiments, the column is a C8 column. In still other embodiments, the column may be a C3 column. It is contemplated that the alkyl moieties may be further modified with for example, polar moieties. For example, it is contemplated that any of the alkyl moieties may also comprise a cyano group or a diphenyl group. Particularly useful columns may be those that are C3-cyano columns. Other preferred columns are C8-diphenyl columns.

In certain embodiments, it may be useful to employ a C8 or C18 stationary phase that has been modified such that the radius of curvature inside the pore (120 A) approached the size of the protein molecule being analyzed. In certain embodiments, methods of the invention are employed for the analysis of antibodies. It is contemplated that in such embodiments employing a stationary phase having a pore size of from about 150 Å to about 350 Å may be particularly useful.

While preferred embodiments employ a C8 or C18 column, it is contemplated that other column matrices and in particular, Poros columns also may be used. In certain embodiments, it may be desirable to perform Poros-RP-LCMS.

c. Mobile Phase

The present invention shows that separation and analysis of high molecular weight proteins is facilitated by the use of a high percentage of a solvent that has a high C-18 eluotropic strength coefficient ($\epsilon°$). An eluotropic strength coefficient of a solvent is a parameter that is used to find the optimum solvent strength for a given solvent on a given solid phase. Thus, the eluotropic strength of a solvent on silica will be different from the strength of that solvent on a C18 column. In the present invention, it is preferred that the mobile phase uses an organic solvent that has an eluotropic strength coefficient of at least 6.0 on a C18 column. The comparative eluotropic strengths of a variety of common organic solvents on different sorbents are provided in Table 1 below.

TABLE 1

Eluotropic Strength of Solvents on Various Sorbents (see The HPLC Solvent Guide, Wiley-Interscience, Paul C. Sadek and LC-GC Vol. 13(3) p222, 1995)

| Solvent | $\epsilon°(Al_2O_3)$ | $\epsilon°(SiOH)$ | $\epsilon°(C18)$ | UV cutoff (nm) |
|---|---|---|---|---|
| Pentane | 0.00 | 0.00 | — | 190 |
| Hexane | 0.00-0.01 | 0.00-0.01 | — | 195 |
| Iso-Octane | 0.01 | 0.01 | — | 215 |
| Cyclohexane | 0.01 | 0.03 | — | 200 |
| Carbon Tetrachloride | 0.17-0.18 | 0.11 | — | — |
| 1-Cholorobutane | 0.26-0.30 | 0.2 | — | 220 |
| Xylene | 0.26 | — | — | 288 |
| Toluene | 0.20-0.30 | 0.22 | — | 284 |
| Chlorobenzene | 0.30-0.31 | 0.23 | — | 287 |
| Benzene | 0.32 | 0.25 | — | — |
| Ethyl Ether | 0.38 | 0.38-0.43 | — | 215 |
| Dicholoromethane | 0.36-0.42 | 0.32-0.32 | — | 295 |
| Chloroform | 0.36-0.40 | 0.26 | — | 245 |
| 1,2-Dichlorethane | 0.44-0.49 | — | — | — |
| Methyl Ethyl Ketone | 0.51 | — | — | 329 |
| Acetone | 0.56-0.58 | 0.47-0.53 | 8.8 | 330 |
| Dioxane | 0.56-0.61 | 0.49-0.51 | 11.7 | 215 |
| 1-Pentanol | 0.61 | — | — | — |
| Tetrahydrofuran | 0.45-0.62 | 0.53 | 3.7 | 212 |
| Methyl t-Butyl Ether | 0.3-0.62 | 0.48 | — | 210 |
| Ethyl Acetate | 0.58-0.62 | 0.38-0.48 | — | 256 |
| Dimethyl Sulfoxide | 0.62-0.75 | — | — | 268 |
| Diethylamine | 0.63 | — | — | — |
| Acetonitrile | 0.52-0.65 | 0.50-0.52 | 3.1 | 190 |
| 1-Butanol | 0.70 | — | — | 215 |
| Pyridine | 0.71 | — | — | — |
| 2-Methoxyethanol | 0.74 | — | — | 210 |
| n-Propyl Alcohol | 0.78-0.82 | — | 10.1 | 210 |
| Isopropyl Alcohol | 0.78-0.82 | 0.60 | 8.3 | 205 |
| Isobutyl Alcohol | — | — | — | 220 |
| Ethanol | 0.88 | — | 3.1 | — |
| Methanol | 0.95 | 0.70-0.73 | 1.0 | 205 |
| Ethylene Glycol | 1.11 | — | — | — |
| Dimethyl Formamide | — | — | 7.6 | 268 |

Propanol is a three carbon alcohol and may be referred to herein as propyl alcohol. Propanol includes n- and iso-propanols, which are useful in RP chromatographic separation of proteins because of their properties as strong alcohols (Benedek et al., *J. Chromatogr.*, v. 317, p. 227-243, 1984; Cohen et al., *Anal. Biochem.*, v. 140, p. 223-235, 1984; Cohen et al., *Anal. Chem.*, v. 56, p. 217-221, 1984; Geng and Regnier, *J. Chromatogr.*, v. 296, p. 15-30, 1984; Oroszlan et al., *Anal. Chem.*, v. 64, p. 1623-1631, 1992; Vidal-Madjar et al., *J. Chromatogr.*, v. 548, p. 81-91, 1991). The C18 eluotropic strength coefficients for iso-propanol (8.3) and n-propanol (10.1) are among the largest for the water miscible organic solvents (Karch et al., *J. Chromatogr.*, v. 122, p. 171-184, 1976). This strength significantly exceeds the values for methanol (1.0), ethanol (3.1) and acetonitrile (3.1).

In addition to the greater displacement properties for the proteins adsorbed on alkyl-bonded surfaces, several studies (Oroszlan et al., *Anal. Chem.*, v. 64, p. 1623-1631, 1992), suggested that propanol facilitates enhanced solvation of proteins in the unfolded state and solvation of the porous n-alkyl silica sorbent. Without being limited to any particular theory or mechanism of action, it is noted that the affinity between the protein and the stationary phase becomes less in the presence of propanol than with acetonitrile. Thus, use of propanol restricts the protein molecules from secondary adsorption after initial desorption (Oroszlan et al., *Anal. Chem.*, v. 64, p. 1623-1631, 1992), thereby allowing elution of the protein in a sharper peak. Hence, when elution of a protein begins after the column has attained a certain concentration of organic solvent, further interactions with the stationary phase, including nonspecific interactions, are minimized with the use of propanols. This property of propanols narrows the chromatographic bandwidth and provides a more efficient and complete elution of the protein. Methanol, ethanol, and n-propanol were found to lower the temperature of denaturation for lysozyme in alcohol-water mixtures, increasingly with higher alcohol concentration and longer alkyl chain (Velicelebi et al., *Biochemistry*, v. 18, p. 1180-1186, 1979). Therefore, n-propanol can denature proteins at lower temperatures.

Thus, in particularly preferred embodiments, n-propanol, ($CH_3$—$CH_2$—$CH_2$—OH) and iso-propanol, $CH_3$—CH(OH)—$CH_3$ are two solvents (alcohols) that are particularly useful in facilitating the LC/MS analysis of antibodies. These solvents have three carbons in their structure, C3. It is noted that the smaller members of the family (methanol) do not provide good resolution and elution of antibodies. Many protein analysis techniques use UV absorption in order to quantify the amount of protein present. Typically, the UV absorption is measured at 215 nm, however, absorption at 254 nm and 280 nm also is sometimes employed. The UV cutoffs of the various solvents employed for the RP-HPLC should therefore be considered when identifying the solvent used for the mobile phase. The higher member of the alcohol family, e.g., iso-butanol have a UV cutoff at 220 nm, rendering it ineffective as a solvent in those methods in which UV detection at 215 nm is necessary, but this may be a useful solvent in RP-HPLC methods of the invention which detect the proteins at a higher UV range (see Table 1 for UV cutoff values of organic solvents). It is interesting that n-propanol and iso-propanol have very high C18 eluotropic values of 10.1 and 8.3, respectively. The C18 eluotropic value for acetonotrile is only 3.1. This parameter is important for the better separation and complete elution of antibodies with propanols that is seen in the preferred examples of the present invention. Dioxane and acetone are the only other solvents that have comparable numbers of 11.7 and 8.8. Thus, dioxane may be another solvent that may be used in the methods of the present invention. On the other hand, acetone is ineffective for those embodiments in which UV detection is to be employed as the UV cutoff for acetone is 330 nm.

It is contemplated that the RP-HPLC methods used in the present invention employ high percentages of the organic solvent. In preferred embodiments, the separation is conducted using the organic solvent present at least at 20% of the mobile phase. The separation may be carried out isocratically (i.e., at a constant ratio of organic:aqueous solvent) or alternatively the separation may be performed at a gradient. Using n-isopropanol as an example of the organic solvent, it is contemplated that in those embodiments where the separation is isocratic, the isopropanol is present at least at 20%, 25%, 30%, 35%, 40%, 45%, 50%, 55%, 60%, 65%, 70%, 75%, 80%, 85% or 90% more of the mobile phase. In particularly preferred embodiments, the solvent is present at 25% of the mobile phase. In alternative embodiments, the RP-HPLC is performed using a gradient elution in which the amount of organic solvent in the mobile phase is increased over the elution period. In such a gradient elution, it is contemplated that the initial percentage of isopropanol is at least 5 and the relative amount of isopropanol is gradually increased to 90%. In preferred embodiments the gradient is 10% to 60% isopropanol between 30 minutes and 60 minutes. In specific embodiments, solvent A has a pH 2.0 mixture of water and TFA, and solvent B has a pH of 2.0 and comprises 70% isopropanol, 20% acetonitrile, 9.9% water and 0.1% TFA. The preferred gradient is run from 0% to 100% solvent B over the period of one hour. It is of note that isopropanol facilitates separation of the proteins components on the HPLC, but it is also advantageous in that it enhances ESI-MS spectra. It is likely that it reduces surface tension of the ES droplets and assists in ion formation (Apffell et al., *J. Chromat.*, 712:177-190, 1995).

In certain embodiments it may be desirable to perform the RP-HPLC at a substantially acidic pH as the kinetics of protein unfolding under RP HPLC conditions at pH 2 on various mobile phases reveals that n-propanol as opposed to acetonitrile provides some protection against protein unfolding by shielding the hydrophobic stationary phase (Benedek, *J. Chromatogr.*, v. 646, p. 91-98, 1993). The nonspecific interactions of the protein with the solid phase due to the negatively charged silanol groups on the solid phase are typically suppressed by maintaining low pH of the mobile phase and adding anionic pairing reagents to mask basic amino acid residues on the surface of protein. Trifluoracetic acid (TFA) is the most popular agent, which satisfies the above two and several other requirements for RP HPLC applications (Winkler et al., *J. Chromatogr.*, v. 347, p. 83-88, 1985). The low pH conditions in many cases also facilitate unfolding of proteins. However, it has been shown that inclusion of TFA in the mobile phase of HPLC suppresses the signal produced in MS analysis. The use of propionic acid has been shown to counteract the effects of the TFA and to enhance the sensitivity of peptide mapping of protein digest using ES-MA (Apffell et al., *J. Chromat.*, 712:177-190, 1995).

Alcohols denature the native state of proteins, and also stabilize the alpha-helical conformation in unfolded proteins and peptides (Hirota, et al., Protein. Sci., 6, 416-421, 1997). Among various alcohols, trifluoroethanol (TFE) and hexafluoroisopropanol (HFIP) are often used because of their high potential to induce such effects. Using CD, Hirota et al. studied the effects of TFE and HFIP as well as reference alcohols, i.e., methanol, ethanol, and isopropanol, on the conformation of bovine beta-lactoglobulin at pH 2. In those studies, upon addition of alcohols, beta-lactoglobulin exhibited a transformation from the native state, consisting of beta-sheets, to the alpha-helical state. The order of effectiveness of alcohols was shown to be: HFIP>TFE>isopropanol>ethanol>methanol. Buchner et al., (Biochemistry, 30, 6922-6929, 1991) showed that the decrease in pH results in the formation of a new, well defined structure of immunoglobulins, which does not exist at higher pH values. Although acid-induced denaturation has been reportedly correlated with the loss of activity for a number of proteins, the conformation state of IgG adopted at low pH was found different from the random coil obtained after denaturation by GuHCl. This low pH structure was reported previously for other proteins and referred to as molten globule state (Ptitsyn et al., FEBS Lett., 262, 20-24, 1990; Kuwajima, Proteins, 6, 87-103, 1989).

Using the techniques provided in the present application, the inventors have shown that the molten globule state of IgG at pH2, elevated temperatures and in the presence of propanol holds helical structure. The appearance of the helical structure at the specified conditions correlates to a reduction in carryover and improved separation of antibodies by reversed-phase chromatography. An elution profile from a reversed-phase column was improved by addition of 3% hexafluoroisopropanol (HFIP) to the mobile phase. CD measurements of the IgG in the mobile phase showed that addition of the small amount of HFIP facilitated formation of helical structure. Thus, peak tailing and carryover of IgGs that is normally seen during RP chromatography is likely due to the presence of different molten globule states of IgG molecules on column. As such, it increased temperature and/or increase in percentage of alcohol results in more uniform folding of IgG molecules. Thus elevating temperature and increasing alcohol in the mobile phase of RP chromatography allows an elimination or decrease in peak tailing and carryover of IgG molecules.

Mass Spectrometry

Mass spectrometry obtains molecular weight and structural information on chemical compounds by ionizing the molecules and measuring either their time-of-flight or the response of the molecular trajectories to electric and/or magnetic fields. The electrospray process is one of the most promising techniques for producing gas phase molecular ions for a wide range of molecular entities. The methods of the present invention employ conventional mass spectrometry techniques known to those of skill in the art. In a conventional electrospray mass spectrometry method, the sample solution is pumped or drawn through an electrospray needle into an electrospray chamber. A potential of up to several kilovolts may be applied to the needle to generate a fine spray of charged droplets. Alternatively, the needle may be held at ground and the opposite electrode at high electric potential. The droplets are typically electrosprayed in the chamber at atmospheric pressure. Optionally, this chamber houses gas lines (e.g., $N_2$) to aid in the nebulization of the solvent stream and the disolvation or evaporation of solvent. The ions generated by the electrospray process are then guided into the mass spectrometer through narrow orifices or nozzles and skimmers by appropriate electric field gradients. Electrospray mass spectrometers are described in further detail in e.g., U.S. Pat. No. 6,673,253 (describes a method of fabricating integrated LC/ESI device and description of ESI mass spectrometry); U.S. Pat. No. 6,642,515 which describes a method and an apparatus for performing electrospray ionization mass spectrometric analysis; U.S. Pat. No. 6,627,883, which is directed to method for analyzing samples in a dual ion trap mass spectrometer but provides background description of ESI-MS; U.S. Pat. No. 6,621,075 which is describes a device for the delivery of multiple liquid sample streams to a mass spectrometer and provides further guidance of the knowledge of those of skill in the art regarding ESI-MS and U.S. Pat. No. 6,188,065 which provides a teaching of the combination of capillary electrophoresis combined with a mass spectrometer. Each of the foregoing patents are incorporated herein by reference in their entirety as showing the general mechanics of a mass spectrometer and methods of introducing samples for mass spectrometry analysis. These are merely exemplary patents providing a general disclosure of mass spectrometers and numerous other mass spectrometers are well known to those of skill in the art. For additional reviews on mass analyzer technology those of skill in the art are referred to Ryan, J. F., "(Editorial), For Openers. MS: Same old, same new," *Today's Chemist at Work* 12, page 7 (2003); Busch, K. L., "Chemical noise in mass spectrometry, Part III-More Mass Spectrometry/Mass Spectrometry," *Spectroscopy* 18, pages 52-55 (2003); Grange, and Sovocool, "Identification of unanticipated compounds by high-resolution mass spectrometry," *Spectroscopy* 18, pages 12, 14, 16, 18, 20, 22, 24 (2003). A description of mass analyzers for LC/MS is provided by Lemiere, F., in *Mass Spectrometry* 17, pages S8, S10-S17, S42 (2002). A glossary of Glossary for Mass Spectrometry may be found at Mass Spectrometry 17, pages S26-S34 (2002).

Commercial sources of mass spectrometers include but are not limited to, Agilent Inc., Bruker Daltonics, Micromass, New Objective, Proxeon, and Thermo Finnegan Corporation. Each of these sources is known to those of skill in the art and can supply the instrumentation for use in the methods of the present invention.

The methods of the present invention are directed to an in-line RP-HPLC-MS analysis of antibodies and other large molecular weight proteins. In these methods the separated protein components of the RP-HPLC step are introduced directly from the HPLC column into the ES ionization chamber of the mass spectrometer. Such in-line introduction of the separated components should preferably prevent the aggregation and precipitation of unfolded proteins and hence facilitate the analysis of antibodies/proteins as compared to off-line mass spectrometry analysis using analogous methods including MALDI techniques.

While it is preferred that the mass spectrometer is an ES-TOF mass spectrometer, it is contemplated that other configurations of mass spectrometers also may be used. Therefore, it is contemplated that the methods of the invention may be performed using, e.g., a time-of-flight (TOF) mass spectrometer, orthogonal TOF mass spectrometer, ion trap (IT) mass spectrometer, Fourier Transform Ion Cyclotron Resonance (FRICR) mass spectrometer, quadrupole (Q) mass spectrometer and magnetic sector mass spectrometer. Such instruments are well known to those of skill in the art and are readily commercially available.

Once the mass spectra are produced, the methods of the present invention employ commercially-available software for the deconvolution of the m/z values to produce MW data of the proteins that have been analyzed. Exemplary software for deconvolution of the mass spectra is MassLynx (Micromass Ltd.)

Additional Protein Separation Techniques

In addition to RP-HPLC, it is contemplated that the present application may advantageously employ additional protein purification techniques for the preparative separation of protein samples prior to application of those samples to the RP-HPLC column. Such protein separation techniques are well known to those of skill in the art. Thus, the methods of the invention may comprise performing an initial protein separation step followed by a RP-HPLC described above. In such embodiments, it is contemplated that the sample eluted from the RP-HPLC step may be analyzed using a mass spectrometry step as described herein above, or alternatively may be analyzed using by other analytical methods, for example x-ray crystallography of the isolated protein fractions. Exemplary methods for using of such combined separation are provided in Example 5. Analytical methods particularly suited for serving the purpose of the initial separation step include size-exclusion chromatography, ion-exchange chromatography, hydrophobic interaction chromatography, isoelectric focusing and capillary electrophoresis.

Ion-exchange chromatography relies on the affinity of a substance for the exchanger, which affinity depends on both the electrical properties of the material and the relative affinity of other charged substances in the solvent. Hence, bound material can be eluted by changing the pH, thus altering the charge of the material, or by adding competing materials, of which salts are but one example. The principle of ion-exchange chromatography is that charged molecules adsorb to ion exchangers reversibly so that molecules can be bound or eluted by changing the ionic environment. Separation on ion exchangers is usually accomplished in two stages: first, the substances to be separated are bound to the exchanger, using conditions that give stable and tight binding; then the column is eluted with buffers of different pH, ionic strength, or composition and the components of the buffer compete with the bound material for the binding sites.

An ion exchanger is usually a three-dimensional network or matrix that contains covalently-linked charge groups. If a group is negatively charged, it will exchange positive ions and is a cation exchanger. A typical group used in cation exchangers is the sulfonic group, SO3—. If an H+ is bound to the group, the exchanger is said to be in the acid form; it can, for example, exchange on H+ for one Na+ or two H+ for one Ca2+. The sulfonic acid group is a strongly acidic cation exchanger. Other commonly used groups are phenolic hydroxyl and carboxyl, both weakly acidic cation exchangers. If the charged group is positive—for example, a quaternary amino group—it is a strongly basic anion exchanger. The most common weakly basic anion exchangers are aromatic or aliphatic amino groups.

The matrix can be made of various materials. Commonly used materials are dextran, cellulose, agarose and copolymers of styrene and vinylbenzene in which the divinylbenzene both cross-links the polystyrene strands and contains the charged groups. Table 2 gives the composition of many ion exchangers.

The total capacity of an ion exchanger measures its ability to take up exchangeable groups per milligram of dry weight. This number is supplied by the manufacturer and is important because, if the capacity is exceeded, ions will pass through the column without binding. Exemplary ion exchangers with their functional groups are identified in the following Table.

TABLE 2

Commercially Available Ion Exchange Resins

| Matrix | Exchanger | Functional Group | Tradename |
|---|---|---|---|
| Dextran | Strong Cationic | Sulfopropyl | SP-Sephadex |
| | Weak Cationic | Carboxymethyl | CM-Sephadex |
| | Strong Anionic | Diethyl-(2-hydroxypropyl)-aminoethyl | QAE-Sephadex |
| | Weak Anionic | Diethylaminoethyl | DEAE-Sephadex |
| Cellulose | Cationic | Carboxymethyl | CM-Cellulose |
| | Cationic | Phospho | P-cel |
| | Anionic | Diethylaminoethyl | DEAE-cellulose |
| | Anionic | Polyethylenimine | PEI-Cellulose |
| | Anionic | Benzoylated-naphthoylated, deiethylaminoethyl | DEAE(BND)-cellulose |
| | Anionic | p-Aminobenzyl | PAB-cellulose |
| Styrene-divinyl-benzene | Strong Cationic | Sulfonic acid | AG 50 |
| | Strong Anionic | | AG 1-Source15Q |
| | Strong Cationic + Strong Anionic | Sulfonic acid + Tetramethylammonium | AG 501 |
| Acrylic | Weak Cationic | Carboxylic | Bio-Rex 70 |
| | Strong Anionic | Trimethylaminoethyl | E. Merk |
| | Strong Anionic | Trimethylamino group | Toso Haas TSK-Gel-Q-5PW |
| Phenolic | Strong Cationic | Sulfonic acid | Bio-Rex 40 |
| Expoxyamine | Weak Anionic | Tertiary amino | AG-3 |

The porosity of the matrix is an important feature because the charged groups are both inside and outside the matrix and because the matrix also acts as a molecular sieve. Large molecules may be unable to penetrate the pores; so the capacity will decease with increasing molecular dimensions. The porosity of the polystyrene-based resins is determined by the amount of cross-linking by the divinylbenzene (porosity decreases with increasing amounts of divinylbenzene). With the Dowex and AG series, the percentage of divinylbenzene is indicated by a number after an X—hence, Dowex 50-X8 is 8% divinylbenzene.

Ion exchangers come in a variety of particle sizes, called mesh size. Finer mesh ion exchange resins have an increased surface-to-volume ratio and therefore increased capacity and decreased time for exchange to occur for a given volume of the exchanger. On the other hand, fine mesh produces a slow flow rate, which can increase diffusional spreading.

There are a number of choices to be made when employing ion exchange chromatography as a technique. The first choice to be made is whether the exchanger is to be anionic or cationic. If the materials to be bound to the column have a single charge (i.e., either plus or minus), the choice is clear. However, many substances (e.g., proteins, viruses), carry both negative and positive charges and the net charge depends on the pH. In such cases, the primary factor is the stability of the substance at various pH values. Most proteins have a pH range of stability (i.e., in which they do not denature) in which they are either positively or negatively charged. Hence, if a protein is stable at pH values above the isoelectric point, an anion exchanger should be used; if stable at values below the isoelectric point, a cation exchanger is required.

The choice between strong and weak exchangers is also based on the effect of pH on charge and stability. For example, if a weakly ionized substance that requires very low or high pH for ionization is chromatographed, a strong ion exchanger is called for because it functions over the entire pH range. However, if the substance is labile, weak ion exchangers are preferable because strong exchangers are often capable of distorting a molecule so much that the molecule denatures. The pH at which the substance is stable must, of course, be matched to the narrow range of pH in which a particular weak exchanger is charged. Weak ion exchangers are also excellent for the separation of molecules with a high charge from those with a small charge, because the weakly charged ions usually fail to bind. Weak exchangers also show greater resolution of substances if charge differences are very small. If a macromolecule has a very strong charge, it may be impossible to elute from a strong exchanger and a weak exchanger again may be preferable. In general, weak exchangers are more useful than strong exchangers.

The Sephadex and Bio-gel exchangers offer a particular advantage for macromolecules that are unstable in low ionic strength. Because the cross-linking in the support matrix of these materials maintains the insolubility of the matrix even if the matrix is highly polar, the density of ionizable groups can be made several times greater than is possible with cellulose ion exchangers. The increased charge density introduces an increased affinity so that adsorption can be carried out at higher ionic strengths. On the other hand, these exchangers retain some of their molecular sieving properties so that sometimes molecular weight differences annul the distribution caused by the charge differences; the molecular sieving effect may also enhance the separation.

The cellulose ion exchangers have proved to be the most effective for purifying large molecules such as proteins and polynucleotides. This is because the matrix is fibrous, and hence all functional groups are on the surface and available to even the largest molecules. In many cases, however, beaded forms such as DEAE-Sephacel and DEAE-Biogel P are more useful because there is a better flow rate and the molecular sieving effect aids in separation.

Buffers themselves consist of ions, and therefore, they can also exchange, and the pH equilibrium can be affected. To avoid these problems, the rule of buffers is adopted: use cationic buffers with anion exchangers and anionic buffers with cation exchangers. Because ionic strength is a factor in binding, a buffer should be chosen that has a high buffering capacity so that its ionic strength need not be too high. Furthermore, for best resolution, it has been generally found that the ionic conditions used to apply the sample to the column (starting conditions) should be near those used for eluting the column. In a specific embodiment, cation exchange (CEX) HPLC was the first dimension of the LC/LC/MS technique utilized to analyze the IgG1 sample. A Dionex Propac 10 weak CEX column was connected to an Agilent 1100 HPLC system.

Size Exclusion Chromatography: Size exclusion chromatography, otherwise known as gel filtration or gel permeation chromatography, relies on the penetration of macromolecules in a mobile phase into the pores of stationary phase particles. Differential penetration of the macromolecules is a function of the hydrodynamic volume of the particles. Size exclusion media exclude larger molecules from the interior of the particles while the smaller molecules are accessible to this volume. The order of elution can be predicted by the size of the protein as a linear relationship exists between elution volume and the log of the molecular weight of the protein being eluted.

Hydrophobic Interaction Chromatography: Certain proteins are retained on affinity columns containing hydrophobic spacer arms. This observation is exploited in the technique of hydrophobic interaction chromatography (HIC). Hydrophobic adsorbents now available include octyl or phenyl groups. Hydrophobic interactions are strong at high solution ionic strength, as such samples being analyzed need not be desalted before application to the adsorbent. Elution is achieved by changing the pH or ionic strength or by modifying the dielectric constant of the eluant using, for instance, ethanediol. A recent introduction is cellulose derivatized to introduce even more hydroxyl groups. This material (Whatman HB1, Whatman Inc., New Jersey, USA) is designed to interact with proteins by hydrogen bonding. Samples are applied to the matrix in a concentrated (over 50% saturated, >2M) solution of ammonium sulphate. Proteins are eluted by diluting the ammonium sulphate. This introduces more water which competes with protein for the hydrogen bonding sites.

A further detailed description of the general principles of hydrophobic interaction chromatography media may be found in U.S. Pat. No. 3,917,527 and in U.S. Pat. No. 4,000,098. The application of HIC to the purification of specific proteins is exemplified by reference to the following disclosures: human growth hormone (U.S. Pat. No. 4,332,717), toxin conjugates (U.S. Pat. No. 4,771,128), antihemolytic factor (U.S. Pat. No. 4,743,680), tumor necrosis factor (U.S. Pat. No. 4,894,439), interleukin-2 (U.S. Pat. No. 4,908,434), human lymphotoxin (U.S. Pat. No. 4,920,196) and lysozyme species (Fausnaugh, J. L. and F. E. Regnier, *J Chromatog.* 359:131-146 (1986)) and soluble complement receptors (U.S. Pat. No. 5,252,216). Suitable hydrophobic interaction chromatography media include, Pharmacia's phenyl-Sepharose, and Tosohaas' butyl, phenyl and ether Toyopearl 650 series resins.

Affinity chromatography is another chromatographic technique, that may be used herein. Examples of commonly used affinity chromatography include immobilized metal affinity chromatography (IMAC), sulfated affinity chromatography, dye affinity chromatography, and heparin affinity. In another example, the chromatographic medium may be prepared using one member of a binding pair, e.g., a receptor/ligand binding pair, or antibody/antigen binding pair (immunoaffinity chromatography). In certain embodiments, affinity chromatography is used to selectively separate IgG antibodies from a mixture of proteins by using protein A or G as a functionality of the stationary phase.

Electrophoresis techniques may be used for the separation of proteins in the first separation step. Such techniques may separate the proteins on the basis of molecular weight e.g., using SDS polyacrylamide gel electrophoresis and/or on the basis of pI e.g., using isoelectric focusing. SDS-PAGE involves complex relationships among several factors including separation length, gel composition, gel pore size, electric field strength, ionic moiety, buffer composition and the mode of migration of the polyion through the gel matrix. In conventional SDS-PAGE separations, biopolymers migrate under the influence of an electric field by tumbling through pores whose average radii are much larger that the radius of gyration of the analyte. Migrating protein samples are thereby size-ordered based on the time required to find a path through the pores of the gel matrix. Larger molecules, i.e. those molecules whose radii of gyration are larger than the average pore size, are impeded and become oriented towards the electric field while migrating through the pores. This process can be induced through increases in either the gel concentration or the applied electric field strength.

Several capillary electrophoresis methods employ narrow-bore capillary columns having large surface-to-volume ratios to effectively dissipate heat. In planar electrophoretic systems, the surface-to-volume ratio is increased through thickness reduction, ideally converging towards capillary dimensions. This is known as "ultra-thin" gel electrophoresis. Rapid biopolymer separation, for example, requires gel-filled separation platforms having a thickness of no more than 0.25 mm. The use of 0.1 mm thick gels for biopolymer separation allows as much as a five-fold increase in electric field strength. Use of polyacrylamide gels having a thickness of 0.025 to 0.1 mm permits resolution of complex mixtures of samples in less than 30 minutes.

Separation matrices for electrophoresis comprised of crosslinked polyacrylamide-polyethylene glycol copolymers achieve size separation of SDS-protein molecules. Linear polymers such as non-crosslinked polyacrylamide, dextran and polyethylene oxides also are effective in producing protein resolution when subjected to an electric field. The use of non-crosslinked polymers has been primarily in high performance capillary electrophoresis applications, although high concentrations of non-crosslinked polymers can be used in planar formats to obtain separation of restriction fragments.

In isoelectric focusing, (IEF) amphoteric molecules such as proteins are separated by electrophoresis in a pH gradient generated between a cathode and an anode. IEF takes advantage of the fact that each protein has a characteristic pH at which it is electrically neutral. This characteristic pH is the isoelectric point (pI) of the protein. Under the influence of an electric field, charged sample components migrate through an electrophoresis medium (a solution or a gel). If a sample component has a net negative charge, it migrates towards the anode. During migration, the negatively charged sample encounters a progressively lower pH, thus becoming more positively charged. Eventually, the pI is reached where the net charge of the sample component is zero. At the pI, migration stops and the sample component is "focused" in a tight zone. Likewise, if a sample component is located at the low pH section of the gradient, it is positively charged and will migrate towards the cathode. In this manner, each sample component migrates to its isoelectric point.

The pH gradient in IEF is provided by carrier ampholytes such as are polyamino-polycarboxic acids that have gradually differing pI values. Ampholyte mixtures are available in various narrow and broad pH ranges. Typically, an anticonvective media such as polyacrylamide or agarose is used as the matrix for IEF. It is also possible to immobilize pH gradients on a suitable matrix such as polyacrylamide or ampholite strips. With immobilized pH gradients, IEF routinely provides a resolution of 0.1 to 0.01 pI units.

Relatively high electric field strengths are necessary to obtain rapid isoelectric focusing. Use of capillary dimensions (i.e. dimensions less than 0.2 mm I.D.) provides efficient dissipation of Joule heat and permits the use of such high field strengths. In capillary dimensions, IEF separations can be carried out in free solution or in entangled polymer networks. IEF and other electrophoresis techniques are further described in e.g., U.S. Pat. No. 5,407,546; and U.S. Pat. No. 6,685,811.

Immobilized pH gradient (IPG) gel with narrow pH ranges are available for use in IEF and produce enhanced resolution of protein separation by pI (Langen et al., *Life Science News* 4:6-8, 2000). Gradient gels and NuPAGE® gels for the SDS-PAGE gel with a variety of gel running buffers also are available and provide further enhancement of the resolution of protein separation by Mw (Molecular Biology Catalog, pp. 649-669].

Samples to be Analyzed

The methods of the present invention are useful for the analysis of proteins, and are particularly useful for analysis of high molecular weight proteins. The methods are also useful for the analysis of protein monomers of high molecular-weight and protein heteromultimers, e.g., antibodies. It is contemplated that these proteins will contain post-translational modifications, such as oligosaccharide moieties and the like. In specific embodiments, the methods of the present invention are used for the analysis of antibodies and antibody domains. In one example, the methods are used for the analysis of proteins having a molecular weight greater than 90 kDa, including intact antibodies, any tertiary protein structure having a molecular weight greater than 90 kDa. It is to be understood that the molecular weight is calculated based on amino acid sequence and includes the known post-translational modifications of the protein, e.g., carbohydrate modification. The methods are applied to characterize the oligosaccharide composition, cleavage, dimer or multimer formation and oxidation of the proteins, structural variants with different disulfide structures, and/or specific amino acids within the protein.

In preferred embodiments, the methods of the invention are used to analyze antibodies and antibody fragments. The sample to be analyzed may comprise an intact antibody comprising an Fc domain and two Fab domains. Alternatively, the methods of the invention are employed to analyze the structure of a portion of an antibody such as for example an $F_C$ domain or one or both of the Fab domains. It is particularly contemplated that the methods of the invention will be useful in the analysis of the products of partial cleavage of an intact antibody. Such cleavage may be performed prior to the RP-HPLC separation. Typical proteolysis will be performed with the use of an enzyme e.g., papain, lyc-C protease or pepsin to yield cleavage of the antibody at the hinge region. Alternatively, the cleavage may employ a reducing agent to reduce the disulfide bonds that connect the two chains of an antibody structure. Such reduction may be achieved using e.g., dithiothreitol, mercaptoethanol, tributylphosphine, and tri(2-carboxyethyl) phosphine hydrochloride. For a review of analytical and preparative methods used in the preparation of antibodies and fragments thereof, those of skill are referred to Josic and Lim: Methods for Purification of Antibodies, *Food Technol. Biotechnol.* 39 (3) 215-226 (2001).

In exemplary embodiments, the limited proteolysis is achieved using endoproteinase Lys-C from a range of 10 to 60 minutes at a pH range of 7.0 to 8.0. The digestion is performed without denaturation at 37° C. with a molar enzyme:protein ratio of 1:150. This produces a few large fragments of the antibody without undue clipping of the protein. The limited proteolysis products are then subjected to RP-HPLC/MS methods described herein. Using this limited proteolysis Fab and Fc fragments at the hinge region of an IgG1 were generated. These methods allowed the detection of a +16 Da increase in the mass of the fragments due to an oxidation of a methionine residue and the detection of a +2 Da increase due to incomplete disulfide bond formation.

The methods of the invention may be used to analyze native proteins, fusion proteins, humanized antibodies, chimeric antibodies, human antibodies, single chain antibodies and the like. In one example, the methods can also be used to analyze any antibody or a fragment thereof that may be as small as 40 kDa, 50 kDa, 55 kDa, 60 kDa, 65 kDa, 70 kDa, 75 kDa, 80 kDa, 85 kDa or greater. In preferred embodiments, the antibody loaded onto the RP-HPLC column is an intact Fab region. In other embodiments, the antibody being analyzed is an (Fab)$_2$ region generated by cleavage of the Fc region of the antibody. Analogously, the methods of the invention also may be used to analyze the Fc region of an antibody generated from such cleavage. In specific embodiments, the antibody being analyzed comprises an intact Fc region and only one intact Fab region.

In addition, the methods of the invention are useful to analyze a protein comprising an antibody Fc region and additional peptides attached thereto, or a protein comprising an Fab region of antibody with additional peptides attached thereto.

The methods of the present invention may be used to analyze recombinant antibodies. Recombinant antibodies can either contain an Fc domain or not contain an Fc domain. In particular, multivalent antibodies may be analyzed using the present invention. As used herein "multivalent antibodies" are recombinant antibody-like molecules that contain binding domains for more than one epitope. For example, such antibody-derived proteins include molecules in which an antibody Fab chain has been fused to binding domains e.g., (Fab-scFv bibodies or tribodies). These molecules are useful intermediate weight recombinant bispecific antibodies that do not containing an Fc portion. Producing antibodies that lack the Fc domain is advantageous because the presence of such a domain on an antibody-related therapeutic molecule tends to increase the serum persistence time of the molecule by protecting it from metabolism in the liver and can also crosslink other cells via its interaction with the Fc receptor, thereby giving rise to toxic side effects due to systemic triggering of immune effector cells. Thus, certain antibody related therapeutic molecules preferably lack the Fc domain. Those of skill in the art are aware of methods to engineer such antibody-related molecules. For example, recombinant antibodies may be produced from a combination of antibody derived building blocks (such as Fc, (Fab')2, Fab, scFv, diabody) with heterodimerizing motifs in order to efficiently create multispecific antibodies.

The methods of the invention are particularly useful in determining the integrity of an antibody and in particular a therapeutic antibody. The antibody is separated and analyzed using the RP-HPLC/MS methods described herein in order to determine the presence of antibody degradation products. The methods described herein allow those skilled in the art to assess the presence of dimers, antibody cleavage products, deamidation, presence of oxidation or formation of N-terminal pyroglutamic acid or scrambling of disulfide bonds of the antibody. These characteristics are all degradations that occur in an antibody and diminish the structural integrity of the antibody.

The methods demonstrated in the examples herein below show the improved chromatographic separation and accurate molecular weight measurements of pharmaceutical antibodies and their degradation products. The method utilizes a high resolution high precision mass spectrometer capable of measuring mass difference between two variants of an antibody that differ by one amino acid residue (e.g., glycine 57 Da) or one sugar moiety (e.g., galactose 162 Da). The mass resolution of the spectrometer should be at least 3000 for a typical IgG antibody with molecular weight of 150 kDa. The mass resolution is calculated as:

Resolution=MW/ΔMW=150 kDa/57 Da≈3000

In certain embodiments, the methods of the present invention are able to detect the change in mass of an antibody or protein of greater than 100 kDa before and after oxidation, i.e., a mass difference of 16 Da. This produces a mass resolution of 10,000 for a typical antibody. The methods of the invention are further illustrated in the examples below.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Analysis of Glycosylation Profiles

Figure 2:
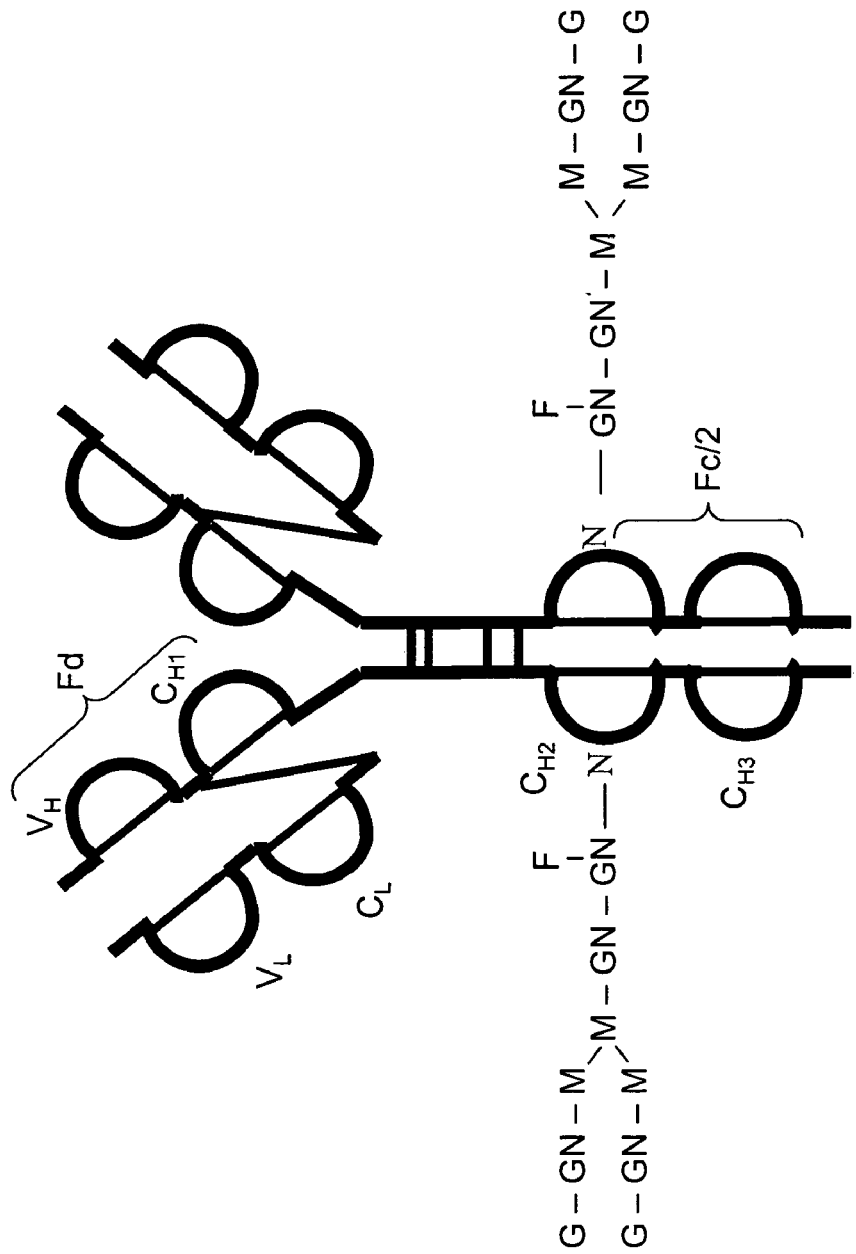
FIG. 2. Structure of a typical recombinant IgG2 monoclonal antibody with attached oligosaccharides. $V_H$ and $V_V$ are variable domains of heavy and light chains. $C_{H1}$, $C_{H2}$, $C_{H3}$, $C_L$ are constant domains. The $C_{H2}$ domains are N-glycosylated with biantennary glycans. Table 3 gives the list of typical oligosaccharide structures.
Figure 3A:
FIG. 3(A) A reversed-phase UV chromatogram of a typical recombinant IgG2 monoclonal antibody. (B) The deconvoluted mass spectrum of the main peak eluting between 12-18 minutes gives glycosylation profile of the intact antibody. The abbreviated peak codes correspond to those of the oligosaccharide structures in Table 3. The glycosylation form 0G-0G is missing all terminal galactose residues and is the most abundant form of this antibody. Each partially resolved peak on the chromatogram (A) gives the same molecular weight value and glycosylation profile as in (B) within the error margin.
Figure 3B:
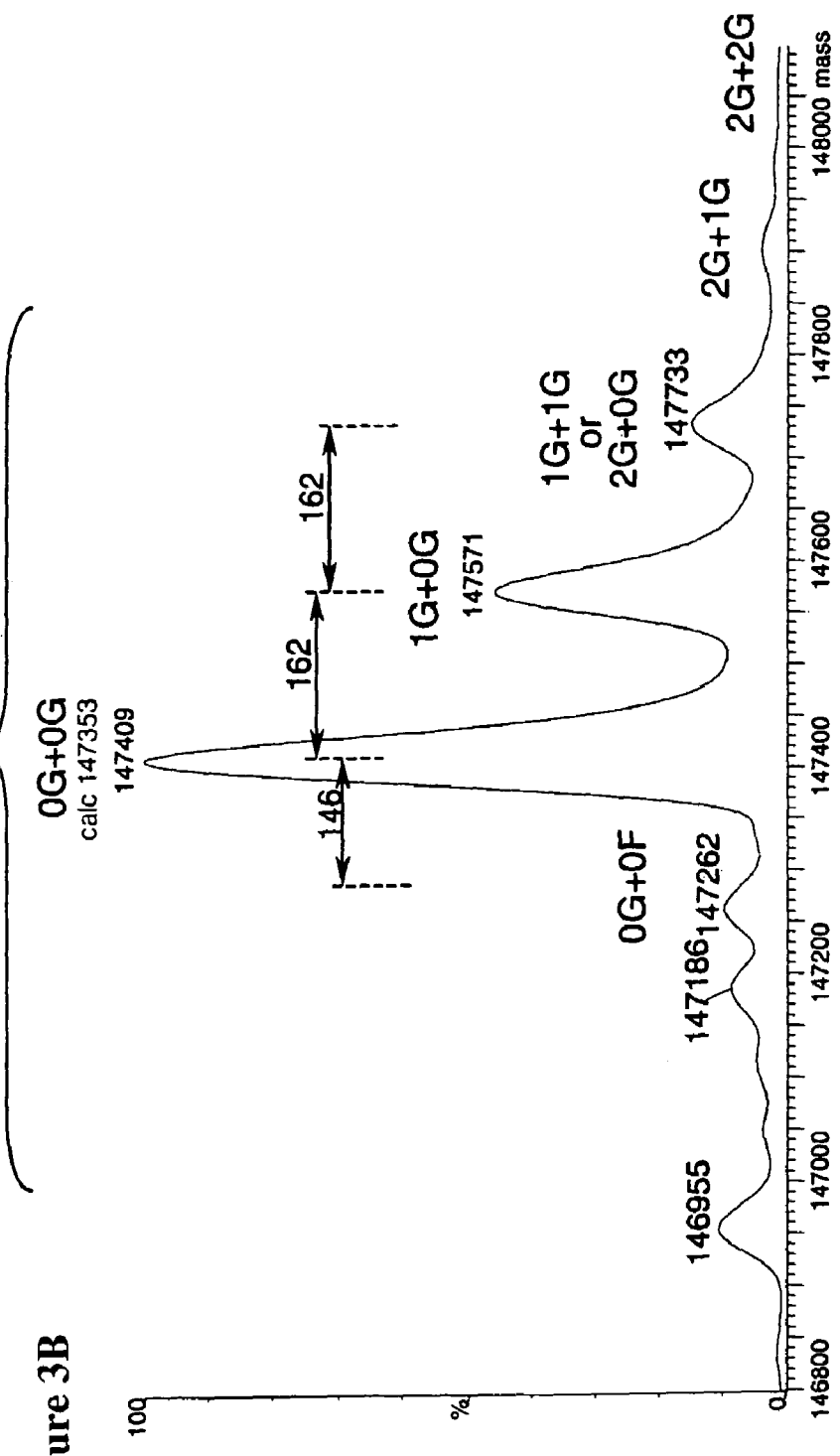
Figure 4:
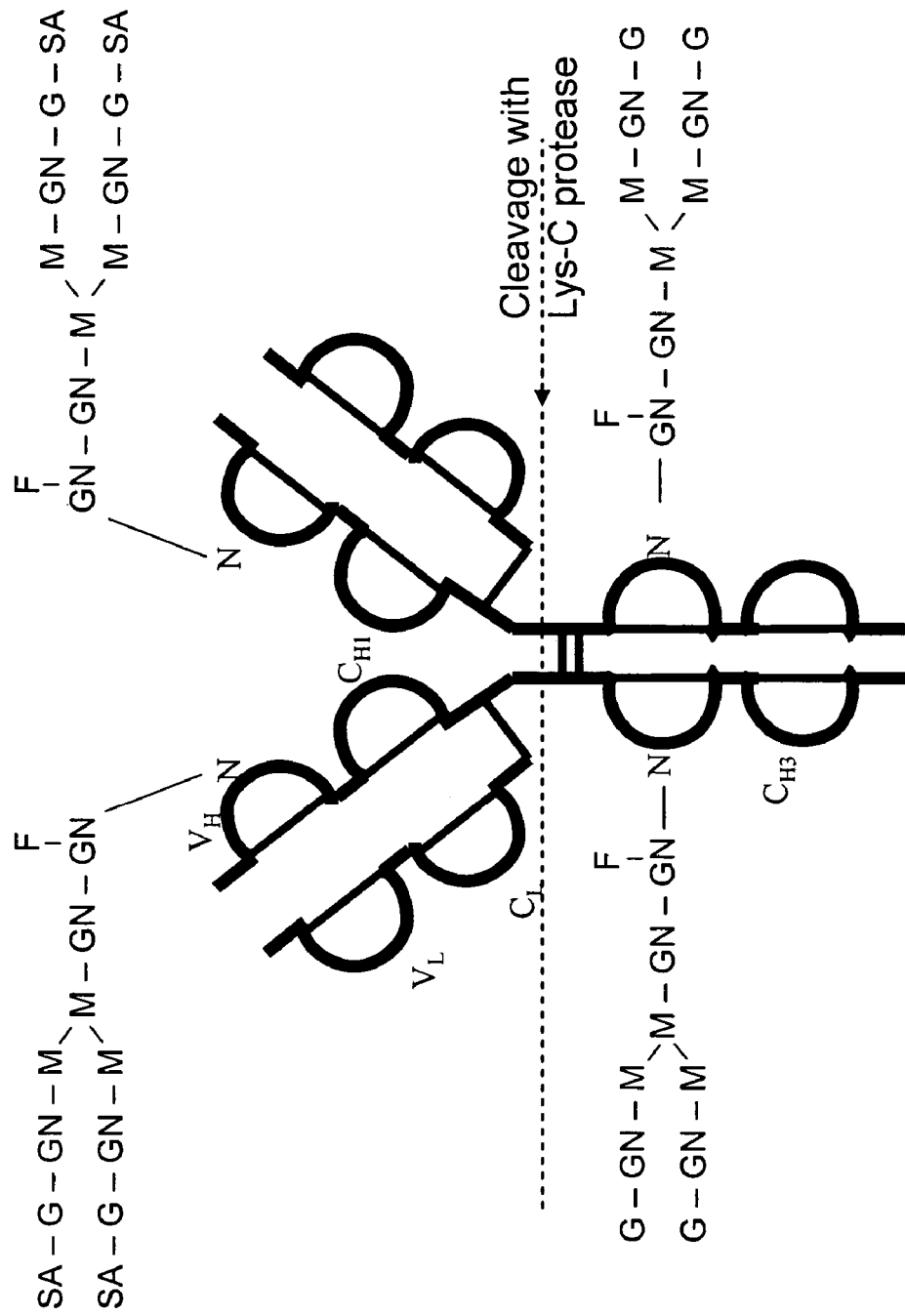
FIG. 4. Structure of an glycosylated recombinant IgG1 monoclonal antibody possessing additional oligosaccharides attached to Fab domain of this antibody. The profile shows presence of additional sugars. After limited proteolysis with Lys-C protease, Fab and Fc fragments were resolved by RP HPLC and their glycosylation profiles were clearly established by an ESI orthogonal TOF mass spectrometer.
Figure 5A:
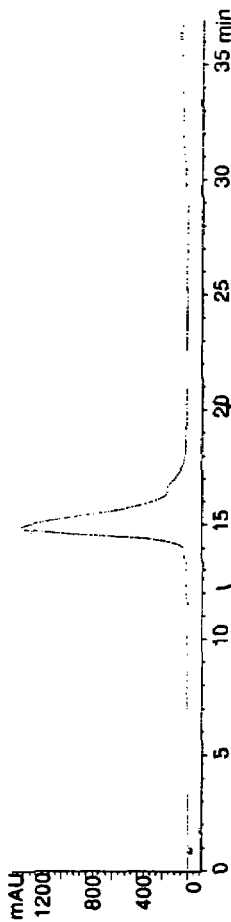
FIG. 5. (A) A reversed-phase UV chromatogram of IgG1 antibody from FIG. 4. (B) The deconvoluted mass spectrum of the main peak eluting between 12-18 minutes give glycosylation profile of the intact antibody. (C) Figure shows the limited proteolysis of IgG1.
Figure 5B:
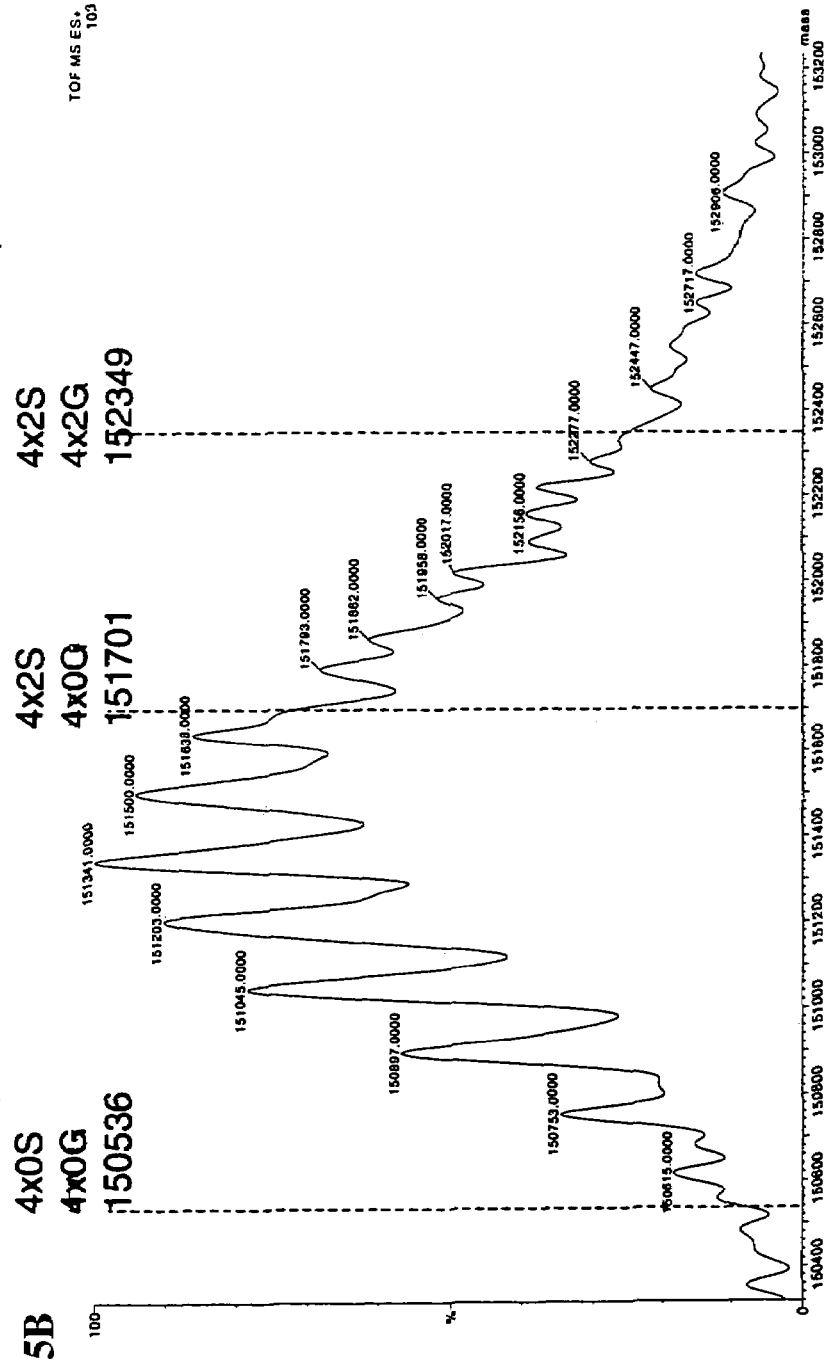
Figure 5C:
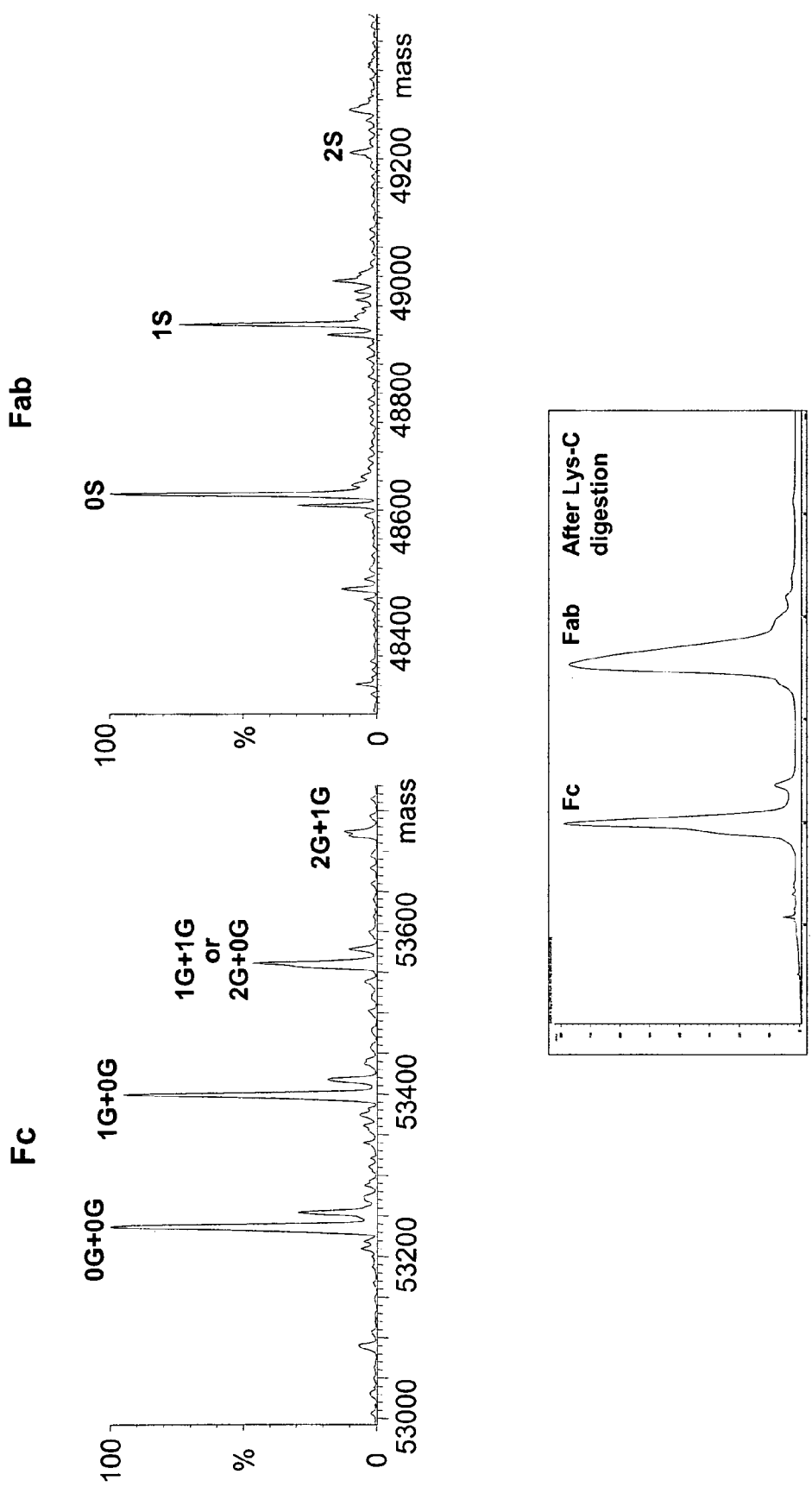

FIG. 2 shows a structure of an IgG2 antibody with attached oligosaccharides. Table 3 presents a range of oligosaccharide structures possible for most antibodies, their molecular weight values and abbreviaton codes. FIG. 3 shows a UV chromatogram of the IgG2 antibody and the deconvoluted electrospray ionization mass spectrum of this antibody with the glycosylation profile. The mass spectrometric profile in FIG. 3B indicates that the most abundant glycosylation form of IgG2 is missing all galactose residues. FIG. 4 is a structure of IgG1 antibody. FIG. 5 shows UV chromatogram of the IgG1 and the deconvoluted electrospray ionization mass spectrum of this antibody with its glycosylation profile. The glycosylation profile of this antibody is more complicated than for IgG2 antibody, because the IgG1 has an additional N-glycosylation in the V$_H$ domain. These additional glycans also have biantennary structure bit with terminal sialic acid residues. In order to provide a clearer interpretation of the complex pattern of peaks observed for IgG1, this molecule was digested with Lys-C protease to smaller fragments: Fc and Fab. The described method allows quick identification of composition and abundances of glycoforms of the pharmaceutical antibodies or their large fragments. It should be understood that the method also may be used in the analysis of any high molecular weight glycoprotein.

TABLE 3

Structures of typical oligosaccharides occurring in antibodies, abbreviation codes and molecular weights. Molecular weights of individual residues are also shown for references.

| Oligosaccharide Structure | Code | Average Mass |
|---|---|---|
| 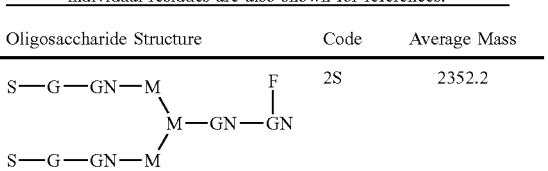 | 2S | 2352.2 |

TABLE 3-continued

Structures of typical oligosaccharides occurring in antibodies, abbreviation codes and molecular weights. Molecular weights of individual residues are also shown for references.

| Oligosaccharide Structure | Code | Average Mass |
|---|---|---|
| S—G—GN—M      F<br>             \\          \|<br>              M—GN—GN<br>           /<br>G—GN—M | 1S | 2060.9 |
| G—GN—M      F<br>       \\         \|<br>        M—GN—GN<br>     /<br>G—GN—M | 0S | 1769.6 |
| G—GN—M      F<br>       \\         \|<br>        M—GN—GN<br>     /<br>G—GN—M | 2G | 1769.6 |
| G—GN—M      F<br>       \\         \|<br>        M—GN—GN<br>     /<br>GN—M | 1G | 1607.5 |
| GN—M      F<br>    \\        \|<br>     M—GN—GN<br>  /<br>GN—M | 0G | 1445.4 |
| GN—M<br>    \\<br>     M—GN—GN<br>  /<br>GN—M | 0F | 1299.2 |

The abbreviations used in the above table are as follows: S: sialic acid=291.3 Da; G: galactose=162.1 Da; GN: N-acetylglucosamine=203.2 Da; M:mannose=162.1 Da and F: fucose=146.1 Da.

Example 2

Identification of Cleavage Sites

Figure 6:
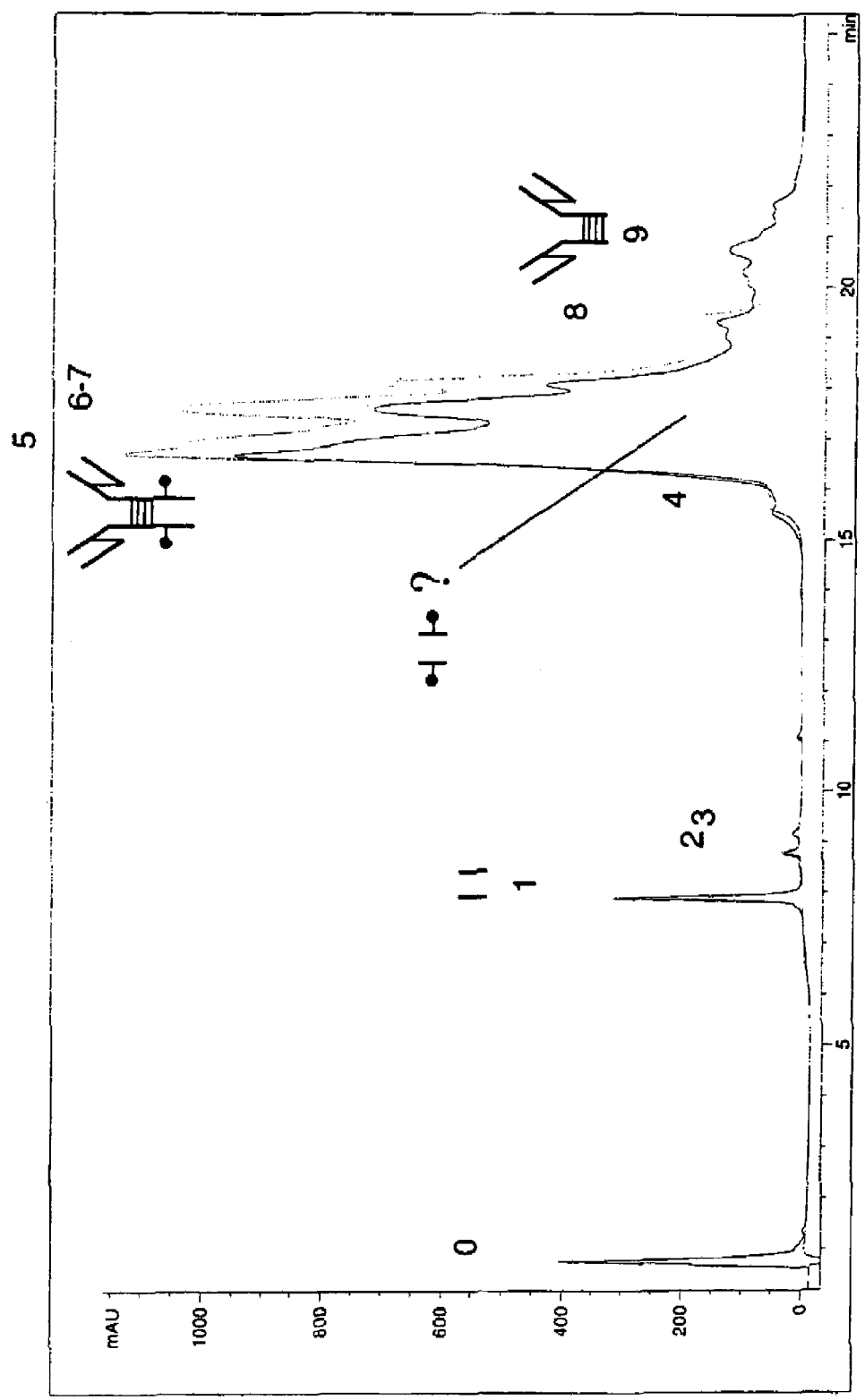
FIG. 6. A reversed-phase UV chromatogram of contaminated and degraded recombinant IgG2 monoclonal antibody after 8 weeks at 37° C. versus control. Peaks 1 and 9 are low MW and high MW fragments of the antibody generated after cleavage.
Figure 7:
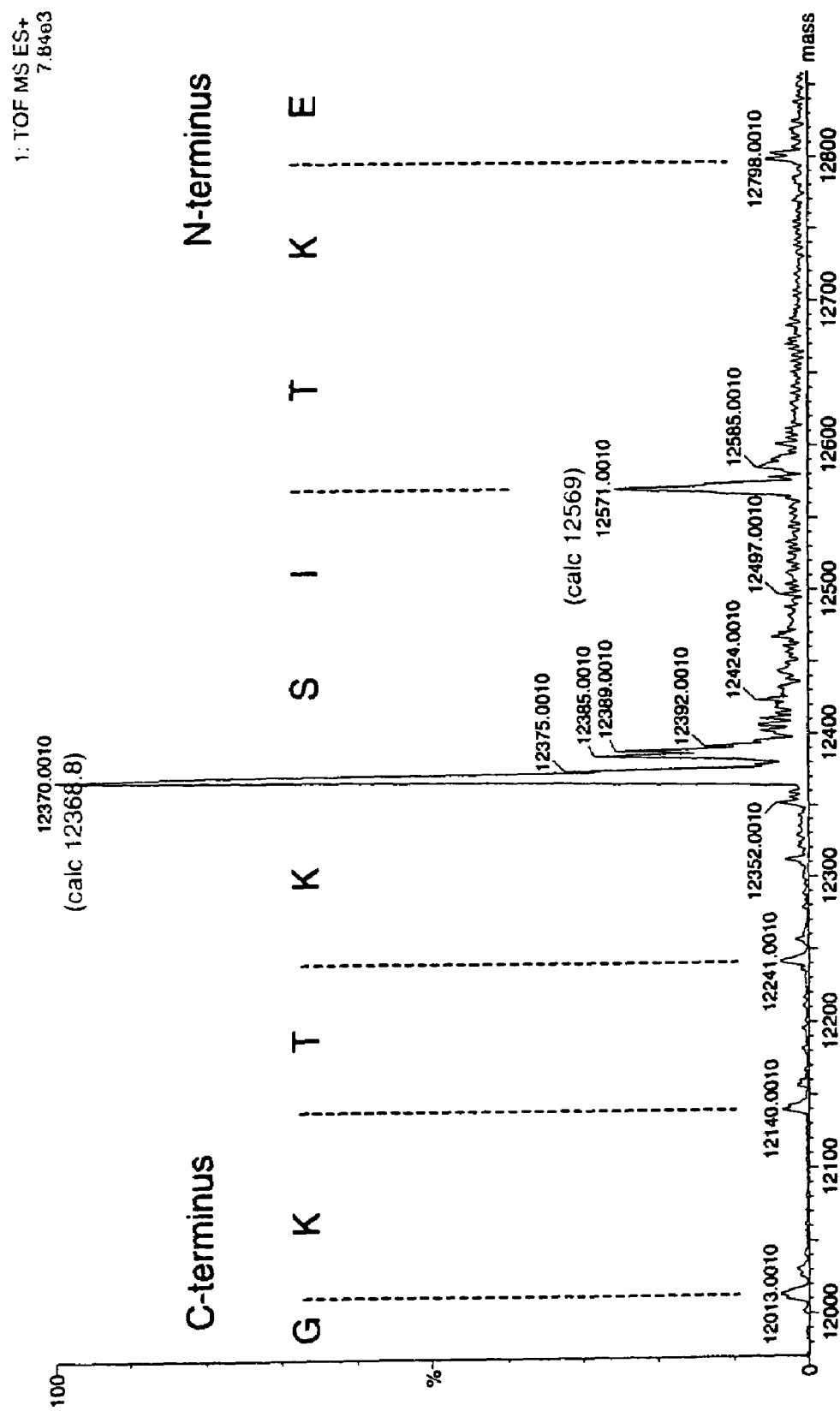
FIG. 7. The deconvoluted electrospray mass spectrum of low MW fragment (peak 1 on FIG. 6) of the IgG2 sample after 8 weeks at 37° C. The measured MW value of the main fragment 12370.0 Da is close (+1 Da or 100 ppm) to the calculated value 12368.8 Da of the heavy chain fragment, S338/K339-G447. In addition to the main cleavage site, several smaller clips were identified by using the minor peaks in the mass spectrum.
Figure 8:
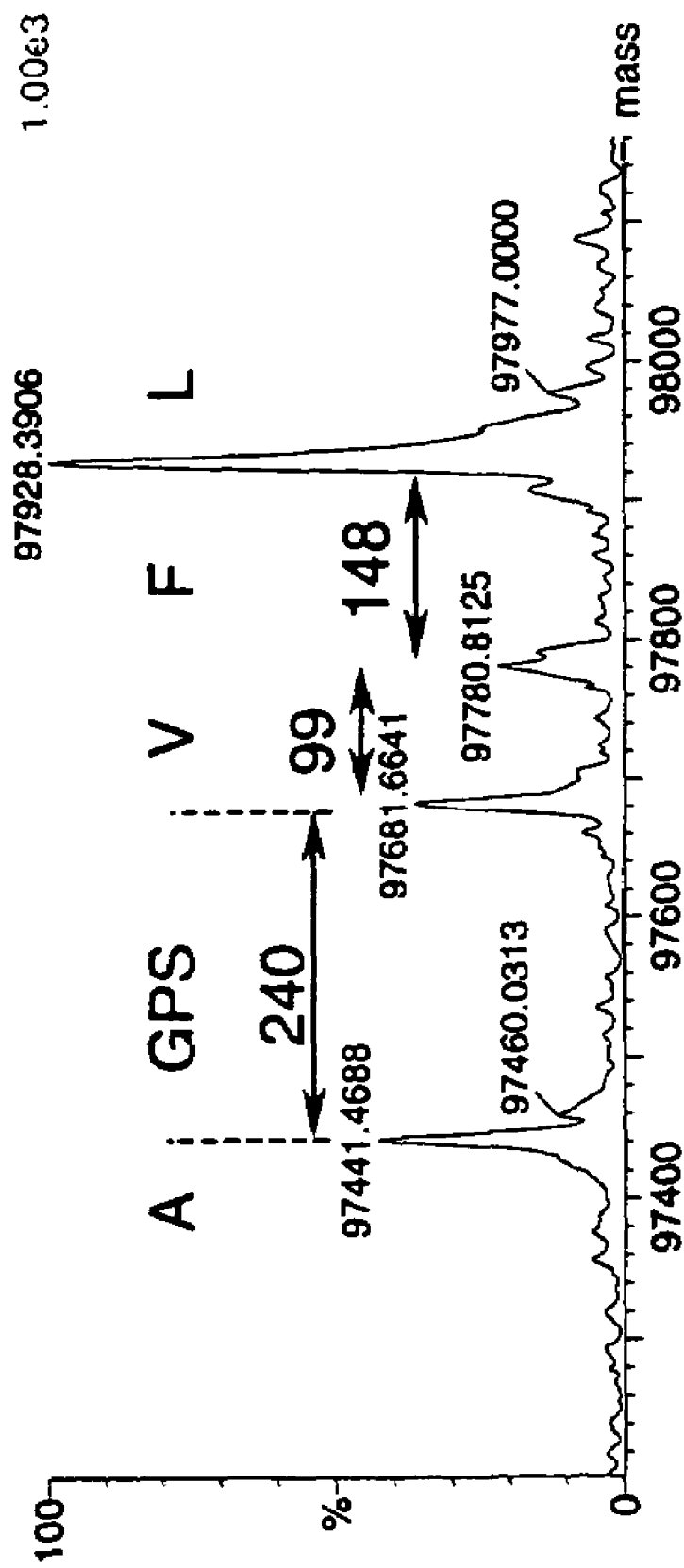
FIG. 8. The deconvoluted electrospray mass spectrum of high MW fragment (peak 9 on FIG. 6) of the IgG2 sample after 8 weeks at 37° C. The measured MW value of the main fragment 97.928 Da is close (+33 Da or 300 ppm) to the calculated value 97,895 Da of the two Fab regions linked at the hinge region. Each Fab region contains a light chain and a heavy chain fragment E001-F242/L243. in addition to the main cleavage site, several smaller clips were identified by using the minor peaks in the mass spectrum.
Figure 9:
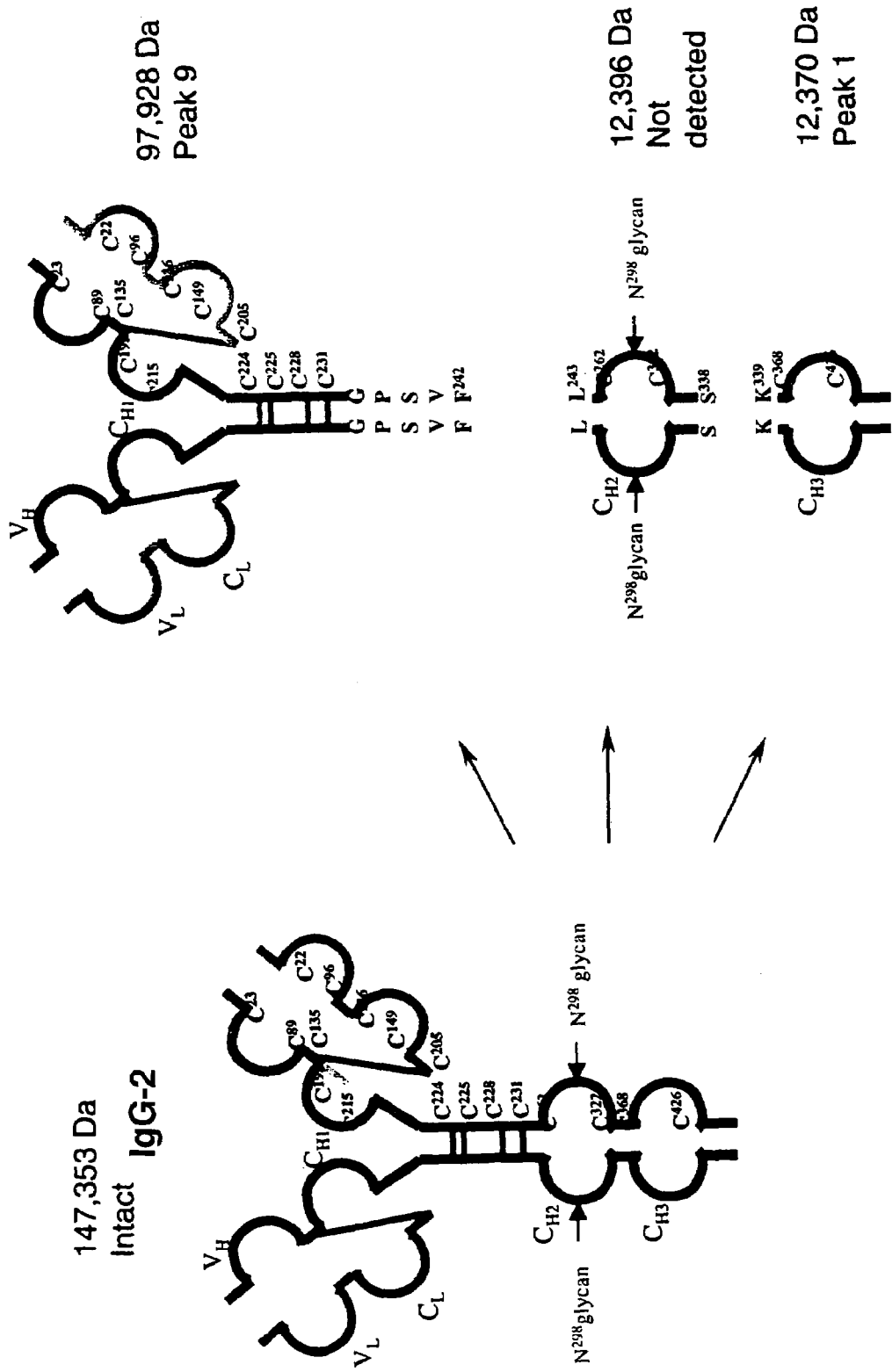
FIG. 9. Total ion current (TIC) chromatograms of another IgG antibody, degraded under accelerated degradation conditions.

Polypeptide bond cleavage is one of the common degradation pathways in proteins, which may take place during manufacturing and delivery of pharmaceuticals such antibodies. It can be caused by metal ions or the presence of residual proteases after purification. Identification of the clipping sites remains an important task because it allows detection and removal of the cause of degradation. FIG. 6 shows the UV chromatogram of IgG2 antibody, which may be contaminated with a protease, after 8 weeks at 37° C. versus a control sample. Peaks 1 and 9 represent cleavage products of the IgG2. The mass spectrum for the main component of IgG2 eluting as peaks 5-7 is shown in FIG. 3. The main component (peaks 5-7) of both the degraded and control samples has the same MW value within the error margin. The masses for peak 1 and 9 cleavage products were identified from the mass spectra presented in FIGS. 7 and 8. Identified clipping sites are between residues F242/L243 and also residues S338/K339 of the amino acid sequence of the heavy chain. FIG. 9 marks the identified cleavage sites of the IgG2 antibody. Three large fragments were generated:12370 Da (peak 1) 97928 Da (peak 9) and glycosylated CH2 containing fragment of 12396 Da (was not detected). Note that in addition to the main clips, mass spectra contain several minor peaks corresponding to the cleavage of the neighboring residues. This feature of degradation provides amino acid sequence information in the vicinity of clip and adds extra confidence to the identification of the cleavage sites. Unlike Edman sequencing of terminal residues, the mass spectrometry-based method of identification of cleavage sites required less time, sample and was performed in-line with the HPLC separation.

The described method also applied in the identification of cleavages of a second IgG1 antibody as discussed below in Example 3.

Example 3

Identification of Dimers

Figure 10:
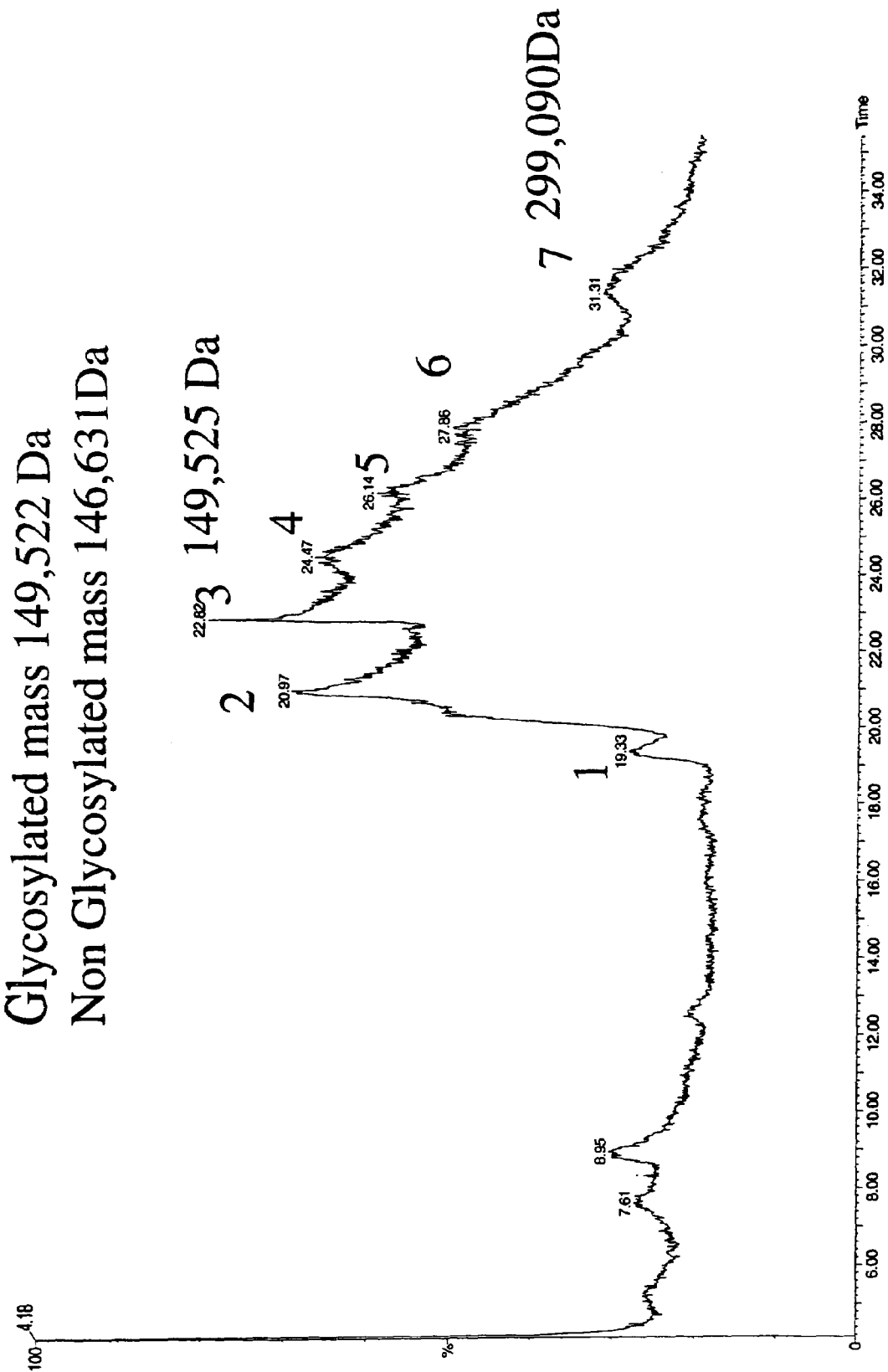
FIG. 10. Total ion current (TIC) chromatograms of an IgG2 antibody.
Figure 11A:
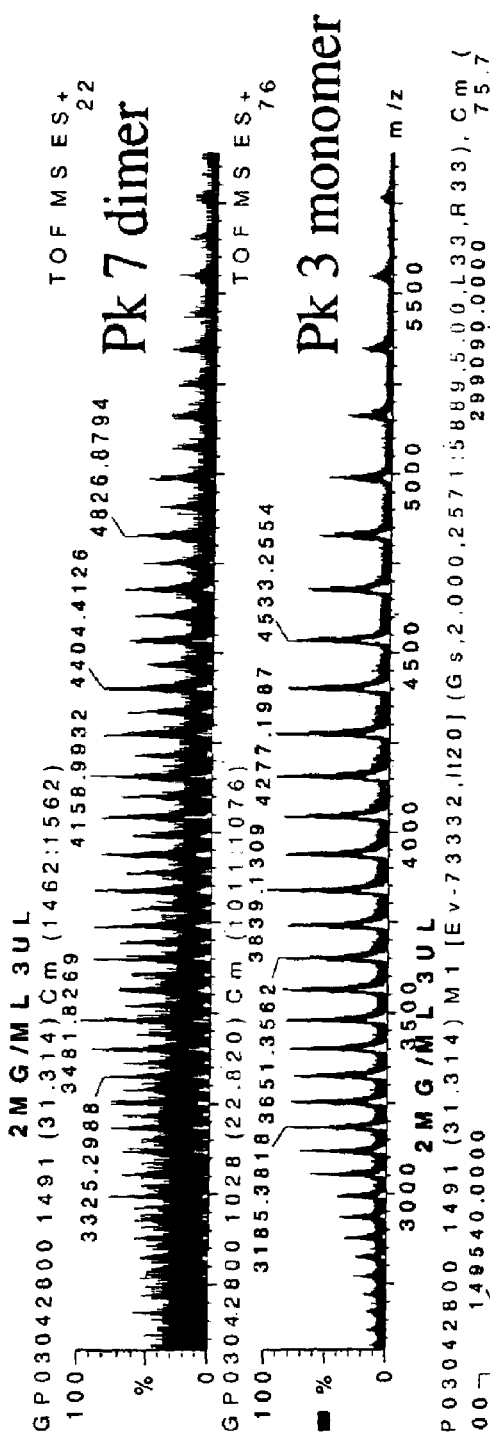
FIG. 11. (A) Electrospray mass spectra and (B) deconvoluted mass spectra of monomer (peak 3 in FIG. 10) and dimer (peak 7 in FIG. 10). The measured MW value of monomer was 149,525 Da as compared to a theoretical calculated value of 149,522 Da (+20 ppm). The measured MW of the dimer was 299,090 Da as compared to a theoretical calculated value of 299,050 Da (+130 ppm).
Figure 11B:
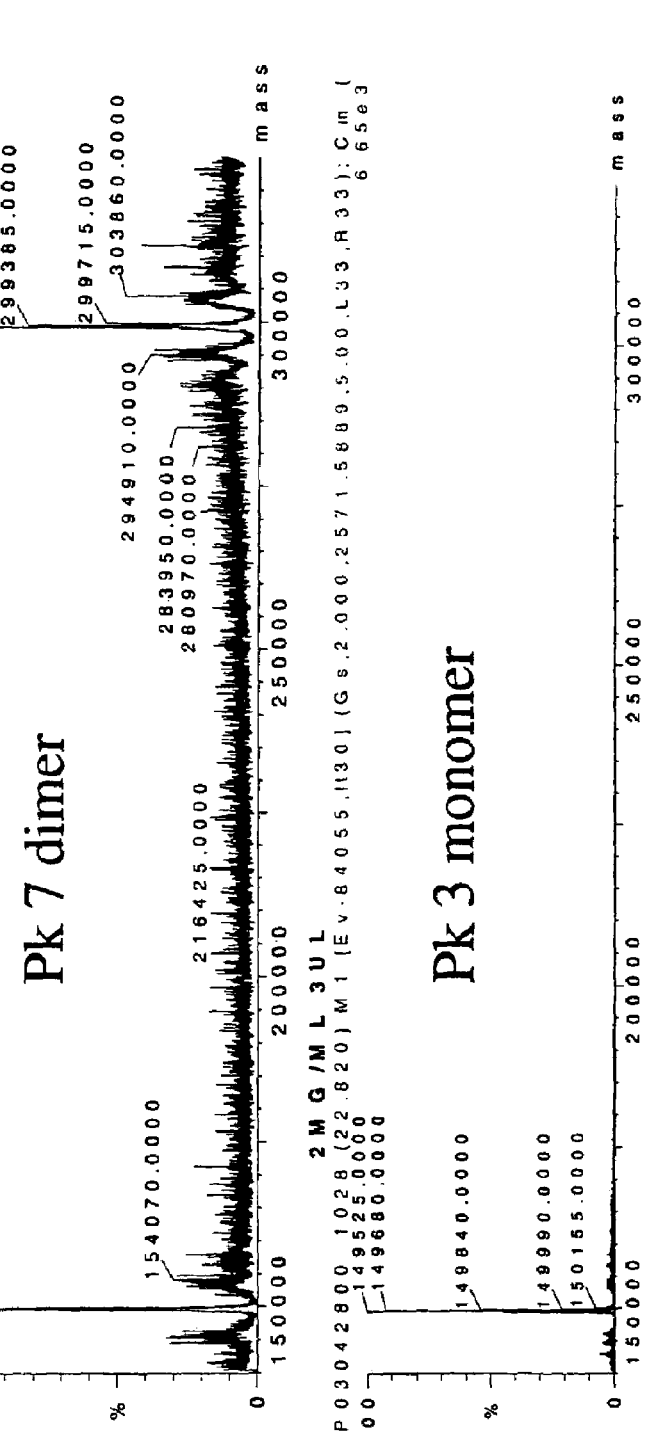

Formation of dimers, aggregates, and associated fragments is another pathway of protein degradation especially in formulation solutions with high protein concentrations. A degraded sample of a second IgG1 antibody was separated by the reversed phase HPLC to separate a main peak and a dimer. The measured MW of the monomer was 149525 Da, as compared to theoretical calculated value of 149522 (+20 ppm). The measured MW of the dimer was 299090 Da, as compared to a theoretical calculated value of 299050 Da (130 ppm). See FIGS. 10 and 11 for more details. This example shows the utility of the method for quick identification of protein aggregates.

Example 4

Identification of Disulphide Bond Rearrangement

There are five immunoglobulin (Ig) classes: IgA, IgD, IgE, IgG and IgM (Brekke and Sandlie, *Nat. Rev. Drug Discov.,* 2:52-62, 2003). Immunoglobulin G (IgG) is the most abundant antibody in serum. The IgG class is also the most stable and has a long half-life in circulation of approximately 20 days. Because of the above and other properties (Brekke and Sandlie, *Nat. Rev. Drug Discov.,* 2: 52-62, 2003), IgG antibody is currently the most popular form (modality) of therapeutic antibody. There are four IgG sub-classes: IgG1, IG2, IgG3 and IgG4. Among them, sub-classes 1 and 2 (IgG1 and IgG2) constitute the majority of the approved and in clinical development antibodies (Brekke and Sandlie, *Nat. Rev. Drug Discov.,* 2: 52-62, 2003). The antibody engineering has gone through several stages of development from mouse antibody to genetically engineered chimeric, humanized and human antibodies. The therapeutic function of antibodies is achieved through complementarity defining regions (CRDs) located in the variable region of heavy chain (VH) and variable region of light chain (VL). The amino acid sequence of CDRs is chosen such a way as to give the antibody a strong affinity towards a target and block the development of a disease.

This example describes application of the newly developed reversed-phase LC/MS method for the analysis of several monoclonal IgG1 and IgG2 antibodies to determine the presence of disulphide bond rearrangement.

Figure 12:
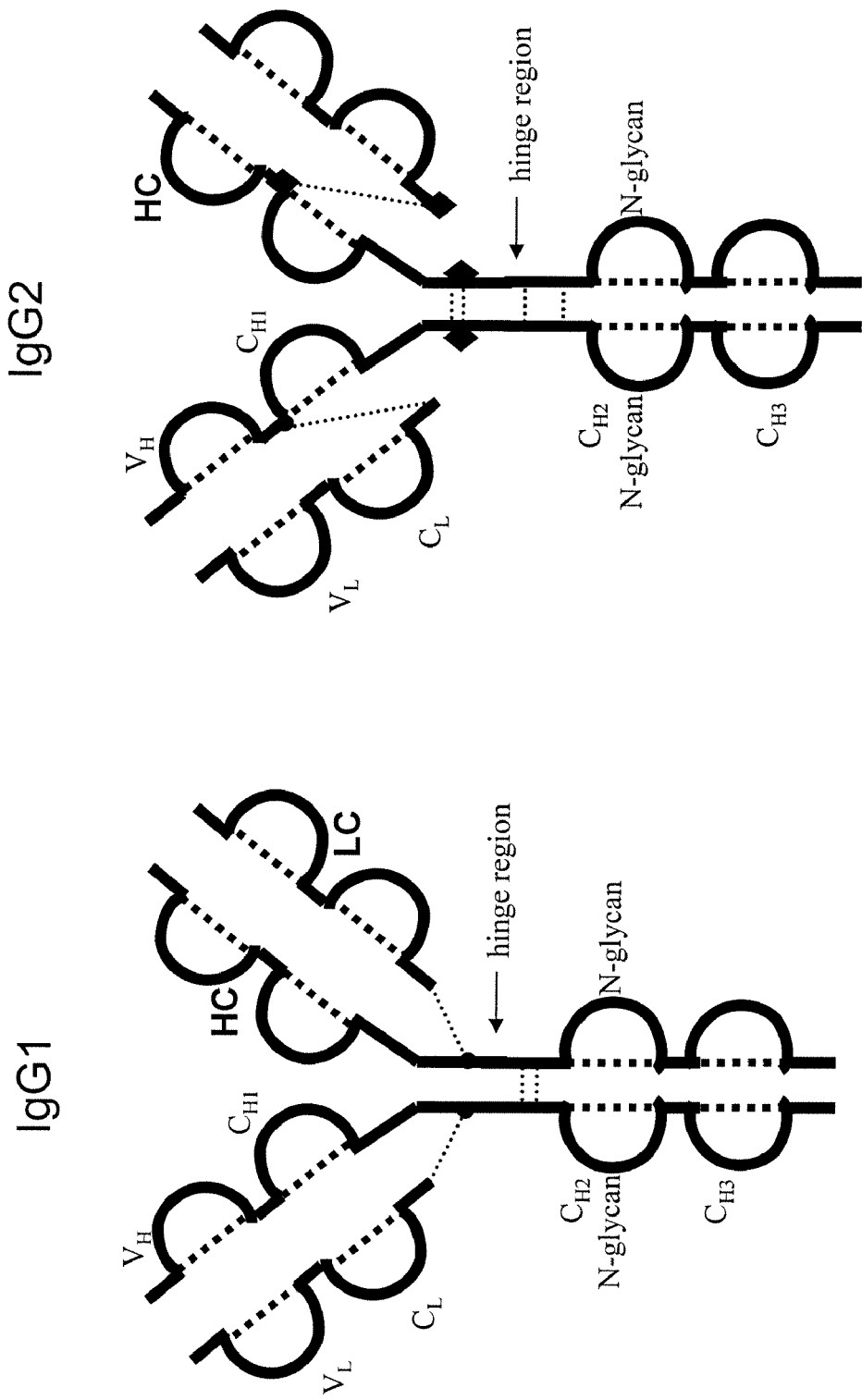
FIG. 12. Comparison of the structures of IgG1 and IgG2 antibodies. Dotted lines depict disulfide bonds between chains. The diamonds with arrows show cysteine residues susceptible to scrambling.

FIG. 12 shows structures of IgG1 and IgG2 antibodies. The immunoglobulin molecule consists of two heavy chains (HCs) and two light chains (LCs). In IgG1, one LC is connected to one HC at the hinge region by a single disulfide bond. Two HCs are connected together by two disulfide bonds closely positioned in the hinge region between domains CH1 and CH2. In IgG2, one LC is connected to one HC between CH2 and CH2 region by a single disulfide bond. Two HCs are connected together by four disulfide bonds closely positioned in the hinge region between domains CH1 and CH2. Although this structure of IgG2 is proposed in the literature, there are no available x-ray crystal structures of the IgG2 hinge region to confirm the disulfide connectivity at the hinge region. In the present example, it is proposed that there are four closely located cysteine residues, labeled in FIG. 12 with diamonds. It is suggested herein that these cysteine residues participate in disulfide rearrangement. The N-terminal (variable) domains of both HCs and LCs contain variable CDRs. These variable CDR domains determine the specificity of interaction of the immunoglobulin with the antigen and are referred to as the VH and VL domains, respectively, for the HC and the LC. The remaining HC and LC domains have conservative sequences and are referred to as the "constant domains". In the HC, the constant domains are conserved regions CH1, CH2, and CH3, and in the LC, the conserved region is termed CL.

Approximately 80% of the amino acid sequence of the CDR is the same for all IgG1 and IgG2 antibodies. However, there are differences at the amino acid level of CDRs. A sequence alignment of a number of antibodies revealed that all the IgG1 antibodies tested had an identical structure in the hinge region, a structure that was characteristic for this subclass of antibodies. All IgG2 antibodies tested had another identical structure of the hinge region that was typical for this latter subclass of antibodies. The structure of the hinge region of IgG1 was different from IgG2.

Figure 13:
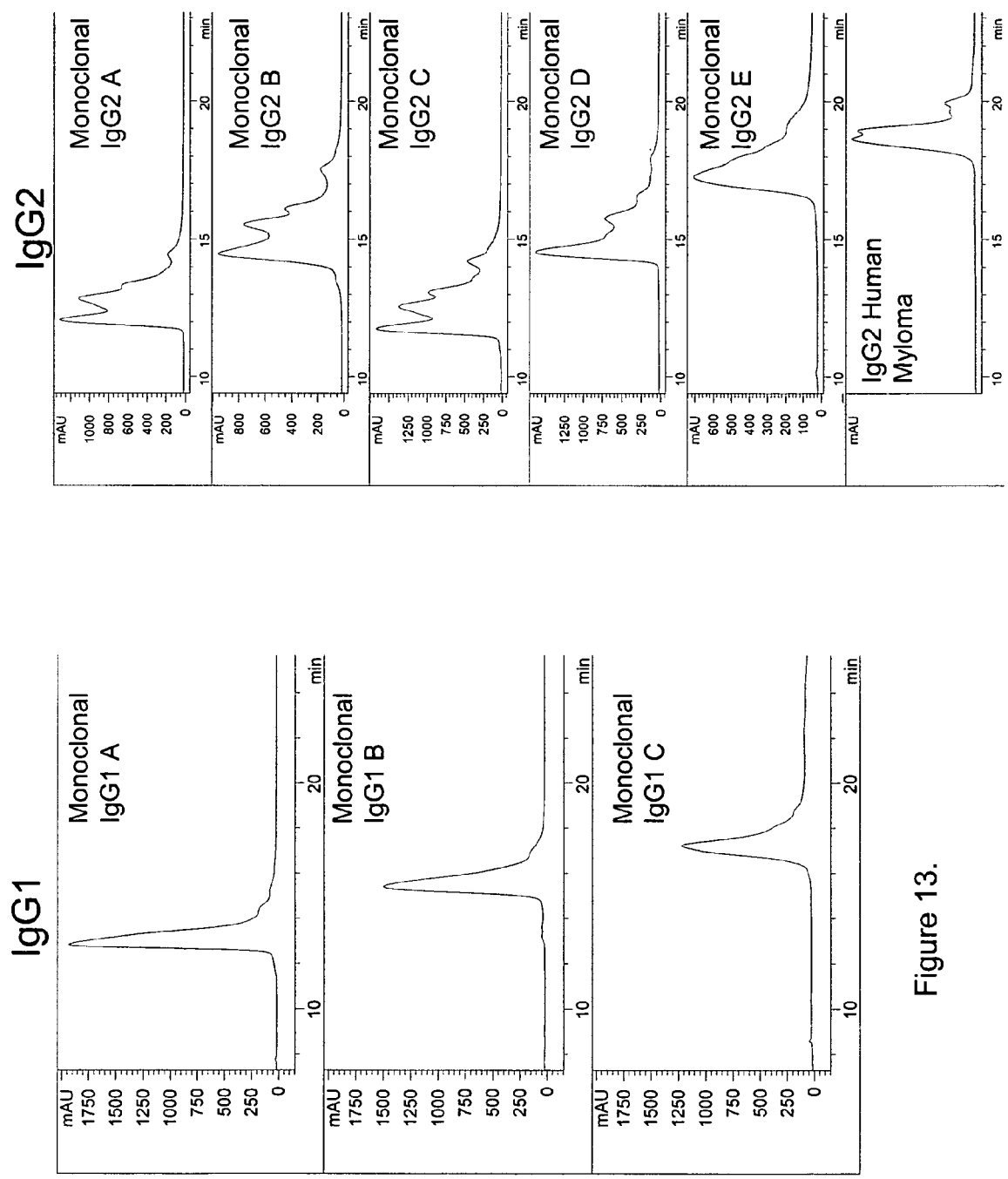
FIG. 13. Reversed-phase chromatograms using UV detection of several IgG2 and IgG1 antibodies.

FIG. 13 shows reversed phase chromatograms using UV detection of several IgG2 and IgG1 antibodies. The IgG2 subclass of antibodies eluted as multiple peaks as compared to the IgG1 antibodies, which elute as a single peak. Thus, there is heterogeneity that is present in IgG2 molecules that is not evident in IgG1 molecules.

Figure 14:
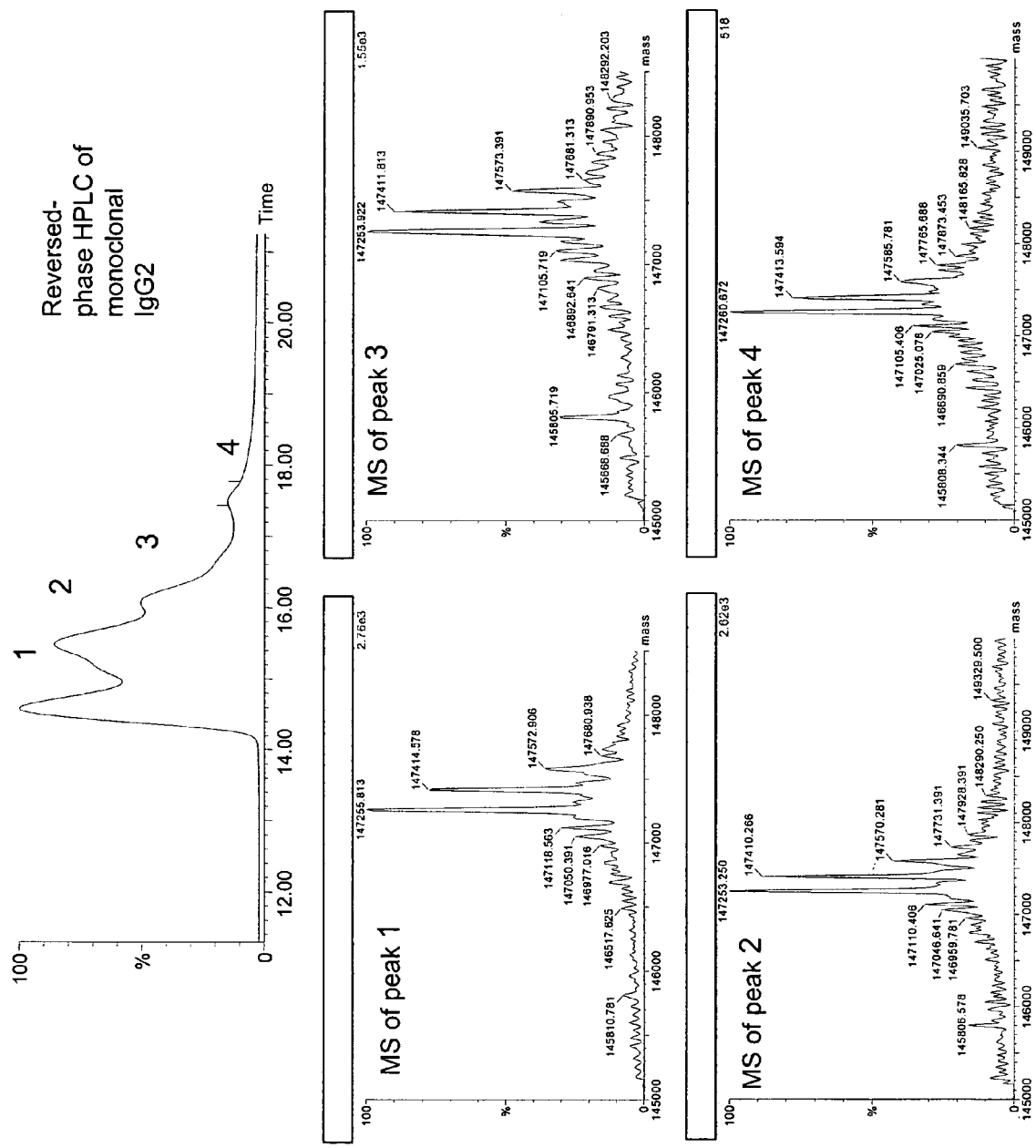
FIG. 14. Deconvoluted electrospray ionization mass spectra of IgG2 variants eluting as chromatographic peaks 1, 2, 3 and 4 in FIG. 13.

FIG. 14 shows deconvoluted electrospray ionization mass spectra of IgG2 variants eluting as chromatographic peaks 1, 2, 3 and 4 in FIG. 13. The mass spectra show several peaks, which are approximately 162 Da apart and represent the loss of galactose residues from the two glycans of antibodies. The largest peak in the mass spectra (G0, MW≈147253) corresponds to the most abundant population of molecules, which lost all galactose residues. The peak to the right has only one galactose and so on. The glycosylation profiles on the mass spectra look similar, which indicates that the IgG2 variants eluting as peaks 1, 2, 3 and 4 are not caused by the heterogeneity in sugar composition of the protein molecules. MW values for the main peaks on all four mass spectra are the same within a few mass units (+/−2 Da) of each other, which is the typical precision of the mass spectrometer used in this study. The fact that MW values of the chromatographic peaks 1, 2, 3, and 4 are so similar allows one to conclude that the unknown modification is associated with very minor MW change or even no change at all. The use of mass spectrometry in the described method allows one to rule out a variety of modifications that were previously reported for monoclonal antibodies because those proposed modifications lead to the relatively larger mass changes. For example, the previously reported modifications of IgG antibodies and corresponding mass changes that can be ruled out include:1) addition or loss of an amino acid residue (smallest is glycine, +/−57 Da); 2) oxidation (+16 Da); 3) addition or loss of a sugar residue (smallest is fucose +/−146 Da); 4) condensation of N-terminal glutamine residues to pyroglutamates (−17 Da).

The mass spectrometric data presented in FIG. 14 (similar MW values) indicate that none of the above modifications can account for the heterogeneity of the IgG2 antibody observed on the reversed-phase chromatograms of FIGS. 12 and 13. Instead, it is proposed that the following modifications may be responsible for the heterogeneity because these following modifications correspond to very small or no MW changes. These latter modifications include:1) deamidation of asparagine residue into aspartic acid residue (+1 Da); 2) isomerization of aspartic acid residue into isoaspartic acid residue (0 Da) reported previously for Herceptin (Harris et al., *J. Chromatogr. B Biomed. Sci. Appl.,* 752: 233-245, 2001); 3) a reduced disulfide bond (+2 Da); 4) disulfide re-arrangement within the cysteine residues at the hinge region of IgG2 (disulfide bond scrambling). The latter modification may present in at least IgG2 proteins, but not for IgG1. The fact that there are several complete x-ray crystal structures of IgG1 available (Saphire et al., *Science,* 293: 1155-1159, 2001) and there are no reports about the IgG2 hinge region also suggests structural heterogeneity at the hinge region. The currently used approach to resolve the disulfide arrangement includes labeling of free cysteine residues at low pH, peptide map of non-reduced protein followed by reduction. This peptide mapping approach involves laborious sample preparation and data interpretation procedures and may introduce artificial disulfide scrambling. The reversed-phase HPLC/MS analyses of intact antibodies presented herein does not require any sample preparation, it is quick and the data are easy to interpret and readily provides a method of monitoring disulfide re-arrangement at the hinge region of IgG2 using RP HPLC/MS of intact antibodies.

Figure 15:
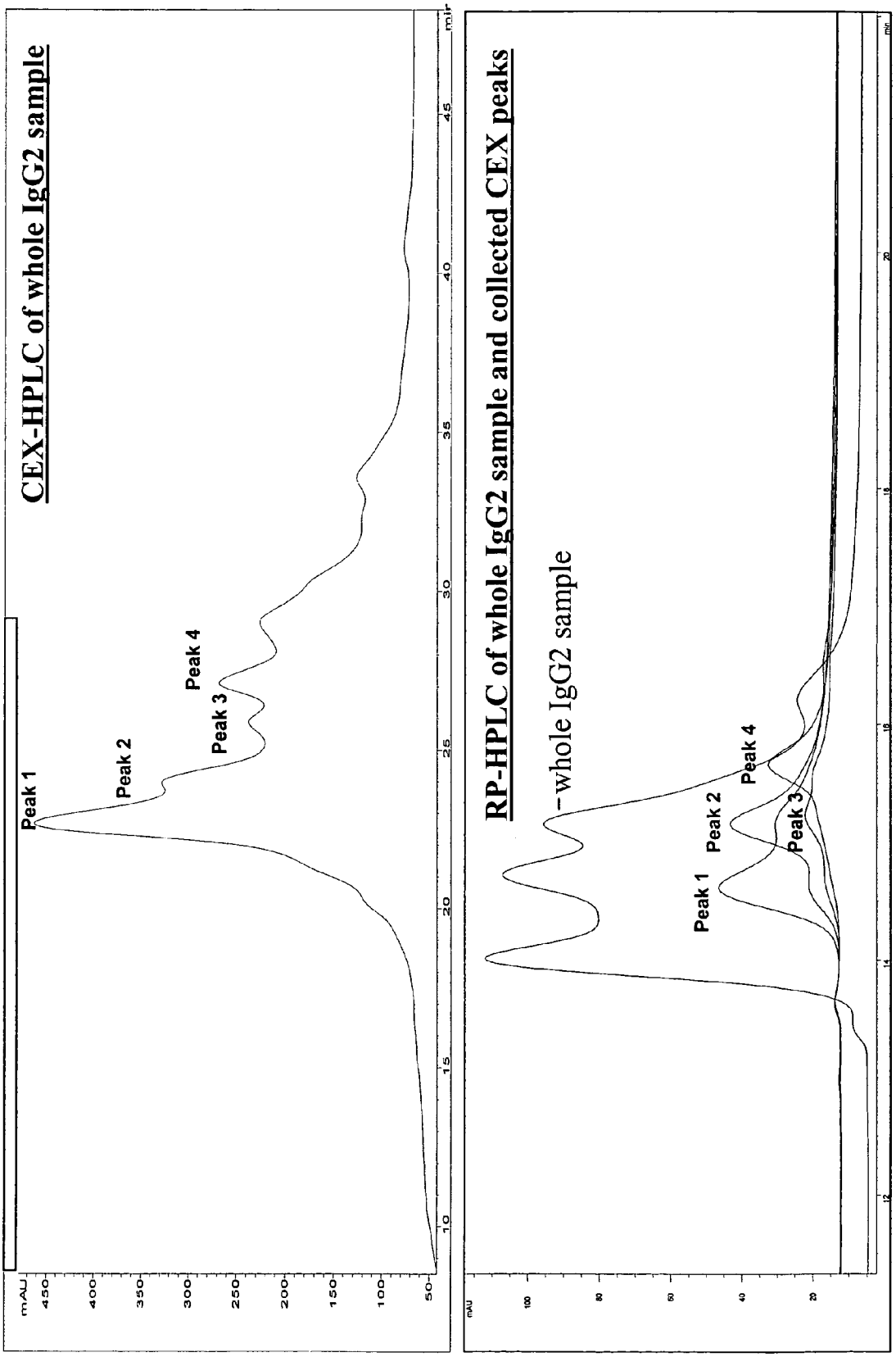
FIG. 15 shows correlation between cation-exchange (CEX) HPLC profile and reversed-phase (RP) HPLC profile.

FIG. 15 shows correlation between cation-exchange (CEX) HPLC profile and reversed-phase (RP) HPLC profile. Four fractions (CEX peak 1, CEX peak 2, CEX peak 3, CEX peak 4) eluting from CEX column were collected and re-injected on RP column. They eluted from the RP column as four peaks (Peak 1, Peak 2, Peak 3 and Peak 4). The elution order and intensity of the individual peaks, Peak 1, Peak 2, Peak 3, and Peak 4 correlated with the partially resolved peaks of the reversed-phase profile of the whole IgG2 sample. CEX-HPLC typically uses sodium and potassium salts, which suppress the electrospray ionization efficiency of the mass spectrometer. Thus, it is contemplated that the CEX chromatography may be performed as a separate step prior to the RP-HPLC. Once RP-HPLC/MS has been used to identify the structure of the antibodies eluted from the CEX, the CEX elution can be used to monitor disulfide re-arrangement at the hinge region of IgG2.

Example 5

Identification of Oxidation and Formation of N-Terminal Pyroglutamic Acid

Oxidation (+16) and the formation of N-terminal pyroglutamic acid from glutamate residues (−17 Da) are common ways of protein degradation during storage and exposure to oxidizing agents including metal ions atmospheric oxygen and light. The combined HPLC/MS method of the invention was used to screen for oxidation of antibodies versus controls. In another study, an antibody with N-terminal pyroglutamic acid residues induced by storage at 37° C. was compared to the control sample. These studies are currently in progress. Initial results indicate that it is possible to detect +16 Da and −17 shifts in two consecutively analyzed samples. When proven successful, this application of the method will provide a powerful tool in identification and quantitation of minor changes in primary structure of pharmaceutical proteins.

The following description exemples methods of identifying and quantifying N-terminal pyroglutamic acid in therapeutic antibodies by reversed phase LC/MS. As discussed above, IgG molecules are glycoproteins that contain two identical copies of LC and HCs interconnected by external disulfide bonds. Although in many IgGs glutamine (Q) is present as an N-terminal residue of a HC, it may be post-translationally modified to a pyroglutamate (pE), thereby blocking the N-terminus from degradation. Cation exchange chromatography (CEX) and IEF electrophoresis have been used to separate antibody variants that contain none, one or two pyroglutamate residues (QQ, QpE, and pEpE, respectively) because pyrolization eliminated the N-terminal amine and generates acidic variants. However, CEX and EIF alone do not provide sufficient specificity to distinguish between the isoforms due to pE formation and the present of other "charged" variants e.g., deamidation, presence of sialic acid and partial unfolding.

As discussed above, the Q/pE conversion is associated with a MW decrease of 17 Da, this is due to the liberation of ammonia ($NH_3$) in converting Q to pE. CEX and IEF are not readily amenable to connection to mass spectrometry, however, as demonstrated above, RP-HPLC can be used in-line with MS analysis. The present example teaches an exemplary method for RP-HPLC/MS of N-terminal pyroglutamic acid in therapeutic antibodies.

An intact IgG antibody is injected directly into the RP-HPLC column. In other embodiments, the same sample was also reduced and alkylated under denaturing conditions using DTT and iodoacetic acid to produce two LCs and HCs per each intact antibody molecule. An Agilent 1100 Capillary HPLC system was connected on-line to a Micromass Q-TOF Micro mass spectrometer through an ESI atmosphere vacuum interface. The ESI-Q-TOF mass spectrometer was set to run in positive ion mode with a capillary voltage of 3400V, sample cone voltage of 80V, m/z range of 800-5500, and mass resolution of 5000. The instrument was tuned an calibrated using multiply charged ions of trypsinogen. The deconvolution of the ESI mass spectra was performed using a MaxEntl algorithm, which is part of the MassLynx software of Micromass.

The selectivity of separation of the QQ, QpE and pEpE variants was increased after the antibody was erduced and alkylated to generate two components: 24 kDa LC and 50 kDa HC. The HC species eluted as two peals with the later peak had a MW value that was 17 Da(+/−1 Da) less than that of the erlier eluting peak. This mass difference indicated that the more retained peak contains HC with pyroglutamte. The peak areas were calculated from the chromatograms of the HPLC. The peak area of the pyroglutmate-HC increased after storage at room temperature in a buffer with pH 5.8. These studies demonstrate that it is possible to rapidly identify and quantify pyroglutamte formation in monoclonal therapeutic antibodies.

In Example 4 herein above there is a comparison of correlation between CEX-HPLC profile and RP-HPLC profiles of an antibody. While CEX-HPLC is not readily used in-line with MS analysis, it is contemplated that it would be desirable to combine CEX-HPLC with a RP-HPLC system of the present invention to achieve superior characterization of antibodies and/or other high molecular weight proteins. In such embodiments, the CEX-HPLC would be preferably be the first separation mode and samples collected from that mode would be applied to the RP-HPLC column. The RP-HPLC column may be a stand-alone RP-HPLC column or may be in-line with a MS apparatus as described above.

Certain aspects of the invention may be further characterized according to the following paragraphs:

Paragraph 1: A method for analysis of a protein in a sample comprising:

(a) preparing a sample comprising said protein for loading onto a chromatography column;

(b) introducing said sample onto a reversed-phase chromatography column;

(c) performing a chromatographic separation to separate said protein from the sample by reversed-phase chromatography on said column, wherein said chromatography column is heated to a temperature of from about 50° C. to about 90° C.; and wherein the mobile phase of said reversed-phase chromatography comprises a water miscible organic solvent having a C18 eluotropic strength coefficient of at least 6.0 and (d) detecting the presence of said protein in an eluate from step (b).

Paragraph 2. The method of paragraph 1, wherein said detecting comprises introducing said eluate from step (b) into the ion source of a mass spectrometer and determining the molecular weight of said protein by mass spectrometry.

Paragraph 3. The method of paragraph 2, wherein said mass spectrometer is an electrospray mass-spectrometer that is in-line with said chromatography column.

Paragraph 4. The method of paragraphs 2 or 3, further comprising identifying the presence or absence of a particular carbohydrate moiety on the protein by comparing the molecular weight data obtained from said sample to molecular weight data from known carbohydrate moieties.

Paragraph 5. The method of paragraph 1, wherein said reversed-phase chromatography is reversed-phase high performance liquid chromatography (HPLC).

Paragraph 6. The method of paragraph 1, wherein said protein is an antibody.

Paragraph 7. The method of paragraph 1, wherein said mobile phase comprises an organic solvent having a C18 eluotropic strength coefficient of at least 8.0.

Paragraph 8. The method of paragraph 1, wherein said mobile phase comprises an organic solvent having a C18 eluotropic strength coefficient of at least 10.0.

Paragraph 9. The method of paragraph 1, wherein said mobile phase comprises an alcohol having between 2 and 4 carbon atoms.

Paragraph 10. The method of paragraph 9, wherein said alcohol is selected from the group consisting of n-propanol, isopropanol, n-butanol and isobutanol.

Paragraph 11. The method of paragraph 1, wherein said mobile phase comprises dioxane.

Paragraph 12. The method of paragraph 1, wherein said chromatography column comprises a silica-based stationary phase derivatized with an alkyl group.

Paragraph 13. The method of paragraph 12, wherein said alkyl group is selected from a C3 to C18 alkyl group.

Paragraph 14. The method of paragraph 13, wherein said alkyl group is a C8 alkyl group.

Paragraph 15. The method of paragraph 13, wherein said alkyl group is a C18 alkyl group.

Paragraph 16. The method of paragraph 13, wherein said alkyl group is a C3 alkyl group.

Paragraph 17. The method of paragraph 14, wherein said C8 alkyl group is derivatized with a diphenyl group.

Paragraph 18. The method of paragraph 16, wherein said C3 alkyl group is derivatized with a cyano group.

Paragraph 19. The method of paragraph 1, wherein said chromatography column comprises a C18 matrix stationary phase.

Paragraph 20. The method of paragraph 1, wherein said chromatography column comprises a C8 matrix stationary phase.

Paragraph 21. The method of paragraph 1, wherein the pH of said mobile phase is between about pH 1.0 to about pH 6.0.

Paragraph 22. The method of paragraph 1, wherein the pH of said mobile phase is between about pH 1.0 to about pH 3.0.

Paragraph 23. The method of paragraph 1 wherein said mobile phase that has a concentration that comprises at least 15% isopropanol at the time of elution of said protein.

Paragraph 24. The method of paragraph 3, wherein said electrospray mass spectrometer comprises a time-of-flight mass analyzer.

Paragraph 25. The method of paragraph 3, wherein said mass spectrometer is an electrospray ionization orthogonal time-of-flight electrospray mass spectrometer.

Paragraph 26. The method of paragraph 1, wherein said mass spectrometer has a mass resolution of at least 3000.

Paragraph 27. The method of paragraph 1, wherein said mobile phase is an isocratic mobile phase comprising at least 20% isopropanol and having an acidic pH.

Paragraph 28. The method of paragraph 1, wherein said mobile phase is an isocratic mobile phase comprising at least 50% isopropanol and having an acidic pH.

Paragraph 29. The method of paragraph 1, wherein said mobile phase is an isocratic mobile phase comprising at least 70% isopropanol and having an acidic pH.

Paragraph 30. The method of paragraph 1, wherein said mobile phase comprises a gradient of isopropanol from 5% isopropanol to 90% isopropanol, wherein said gradient is established over a period of 30 minutes.

Paragraph 31. The method of paragraph 1, wherein said mobile phase comprises a gradient of isopropanol from 10% isopropanol to 60% isopropanol, wherein said gradient is established over a period of 30 minutes.

Paragraph 32. The method of paragraph 31, wherein said gradient is established comprising introducing a mixture of a first solvent A and a second solvent B as the mobile phase for said chromatographic separation, wherein said first solvent A comprises a mixture at pH 2.0 of water and trifluoracetic acid (TFA) and said second solvent B comprises a mixture at pH 2.0 of 70% isopropanol, 20% acetonitrile 9.9% water and 0.1% TFA.

Paragraph 33. The method of paragraph 1, wherein said high molecular weight protein has a molecular mass of about 90 kDa.

Paragraph 34. The method of paragraph 1, wherein said high molecular weight protein is cleaved to protein fragments prior to analysis.

Paragraph 35. The method of paragraph 1, wherein said high molecular weight protein has been cleaved to protein fragments having a molecular mass of 80 kDa.

Paragraph 36. The method of paragraph 1, further comprising an additional protein separation step prior to said HPLC.

Paragraph 37. The method of paragraph 36, wherein said additional separation step comprises size-exclusion chromatography, ion-exchange chromatography, hydrophobic interaction chromatography, affinity chromatography, or capillary electrophoresis.

Paragraph 38. A method for analyzing an antibody or a fragment thereof said method comprising:

(a) preparing a sample comprising said antibody or fragment thereof for loading onto a high performance liquid chromatography (HPLC) column;

(b) separating said antibody or fragment thereof from said sample by reversed-phase HPLC on said column, wherein the eluate from said reversed-phase HPLC is introduced into a device that determines the presence of the antibody or antibody fragment and, wherein said device is in-line with said HPLC column; and (c) detecting the presence of said antibody or fragment thereof;

wherein said HPLC column is heated to a temperature of from about 50° C. to about 90° C.; and wherein the mobile phase of said reversed-phase HPLC comprises a water miscible organic solvent having a C18 eluotropic strength coefficient of at least 6.0.

Paragraph 39. The method of paragraph 38, wherein said device that determines the presence of the antibody or antibody fragment is a mass spectrometer positioned in-line with said HPLC column such that the eluate from the reversed-phase column is introduced into the ion source of said mass spectrometer, and wherein said mass spectrometer provides mass fragmentation data for said antibody or fragment thereof.

Paragraph 40. The method of paragraph 38, wherein said antibody comprises an antibody having an Fc region and two Fab regions.

Paragraph 41. The method of paragraph 40, wherein said antibody is an isotype selected from the group consisting of IgG1, IgG2, IgG3, and IgG4.

Paragraph 42. The method of paragraph 38, wherein said antibody is a single chain antibody.

Paragraph 43. The method of paragraph 38, wherein said antibody is a humanized antibody.

Paragraph 44. The method of paragraph 38, wherein said antibody is a humanized IgG2 antibody.

Paragraph 45. The method of paragraph 38, further comprising the step of subjecting said sample containing said antibody to limited proteolysis.

Paragraph 46. The method of paragraph 38, wherein said step of limited proteolysis is conducted prior to loading said sample on said HPLC column.

Paragraph 47. The method of paragraph 46, wherein said limited proteolysis comprises reducing the disulfide bonds in said antibody or fragments thereof.

Paragraph 48. The method of paragraph 47, wherein said reducing the disulfide bonds comprises contacting said sample with a chemical reducing agent.

Paragraph 49. The method of paragraph 48, wherein said chemical reducing agent is selected from the group consisting of dithiothreitol, mercaptoethanol, tributylphosphine, and tri(2-carboxyethyl)phosphine hydrochloride.

Paragraph 50. The method of paragraph 46, wherein said step of limited proteolysis comprises subjecting said intact antibody to proteolysis with papain, pepsin, or Lys-C protease.

Paragraph 51. The method of paragraph 38, wherein said mass spectrometry step is performed on a mass spectrometer selected from the group consisting of a time-of-flight (TOF) mass spectrometer, orthogonal TOF mass spectrometer, ion trap (IT) mass spectrometer, Fourier Transform Ion Cyclotron Resonance (FRICR) mass spectrometer, quadrupole (Q) mass spectrometer and magnetic sector mass spectrometer.

Paragraph 52. A method of determining the presence of an antibody degradation product in an antibody sample, said method comprising:

a. performing RP-HPLC on said antibody sample under conditions wherein the HPLC column is heated to a temperature of from about 50° C. to about 90° C.; and wherein the mobile phase of said reversed-phase HPLC comprises a water miscible organic solvent having a C18 eluotropic strength coefficient of at least 6.0, and b. determining the molecular weight data of the components of the antibody sample using ESI-MS.

Paragraph 53. The method of paragraph 52, further comprising correlating said molecular weight data from said antibody sample to data obtained from known protein standards.

Paragraph 54. The method of paragraph 53, wherein said known protein standard is an antibody sample that has not undergone degradation.

Paragraph 55. The method of paragraph 53, wherein said degradation product is selected from the group consisting of a dimer, a cleavage product, oxidation of the antibody sample, deamidation of the antibody sample, N-terminal pyroglutamation of the antibody sample and disulfide bond scrambling of the antibody sample.

Paragraph 56. A method of determining disulphide bond rearrangement of an IgG2 sample, said method comprising:

a. performing RP-HPLC on said IgG2 sample under conditions wherein the HPLC column is heated to a temperature of from about 50° C. to about 90° C.; and wherein the mobile phase of said reversed-phase HPLC comprises a water miscible organic solvent having a C18 eluotropic strength coefficient of at least 6.0;

b. detecting the presence of heterogeneous peaks from said RP-HPLC of said IgG2 sample; and c. determining the molecular weight data of the components of the heterogeneous peaks of said RP-HPLC of said IgG2 sample using ESI-MS, wherein identical or similar molecular weight data is indicative of disulphide bond rearrangement in said IgG2 sample.

Paragraph 57. The method of paragraph 56, wherein said similar molecular weight data comprises a mass difference of two mass units.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A method of determining the presence of an antibody degradation product in an antibody sample, said method comprising:

a. performing RP-HPLC on said antibody sample under conditions wherein the HPLC column is heated to a temperature of from about 50° C. to about 90° C.; and wherein the mobile phase of said reversed-phase HPLC comprises a water miscible organic solvent having a C18 eluotropic strength coefficient of at least 6.0, and b. determining the molecular weight data of the components of the antibody sample using ESI-MS.

2. The method of claim 1, further comprising correlating said molecular weight data from said antibody sample to data obtained from known protein standards.

3. The method of claim 1, wherein said known protein standard is an antibody sample that has not undergone degradation.

4. The method of claim 1, wherein said degradation product is selected from the group consisting of a dimer, a cleavage product, oxidation of the antibody sample, deamidation of the antibody sample, N-terminal pyroglutamation of the antibody sample and disulfide bond scrambling of the antibody sample.

* * * * *